US 9,580,370 B2

(12) United States Patent
Hottovy et al.

(10) Patent No.: US 9,580,370 B2
(45) Date of Patent: Feb. 28, 2017

(54) ETHYLENE RECOVERY BY ABSORPTION

(71) Applicant: Chevron Phillips Chemical Company LP, The Woodlands, TX (US)

(72) Inventors: John D. Hottovy, Kingwood, TX (US); Ai-fu Chang, Houston, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 15/189,453

(22) Filed: Jun. 22, 2016

(65) Prior Publication Data

US 2016/0297729 A1 Oct. 13, 2016

Related U.S. Application Data

(63) Continuation of application No. 14/877,590, filed on Oct. 7, 2015, now Pat. No. 9,399,608, which is a
(Continued)

(51) Int. Cl.
*C07C 7/11* (2006.01)
*C07C 7/156* (2006.01)
(Continued)

(52) U.S. Cl.
CPC .............. *C07C 7/11* (2013.01); *B01D 53/1487* (2013.01); *B01D 53/1493* (2013.01);
(Continued)

(58) Field of Classification Search
CPC ............ B01D 19/1818; B01D 53/1487; B01D 53/1493; C08F 6/001; C07C 7/11
(Continued)

(56) References Cited

U.S. PATENT DOCUMENTS 2,610,704 A 9/1952 Patterson
2,921,053 A 1/1960 Dye
(Continued)

FOREIGN PATENT DOCUMENTS

EP 1603955 B1 * 5/2006 ................ C08F 2/01
EP 2018899 A1 1/2009
(Continued)

OTHER PUBLICATIONS

Peacock, Andrew J., Handbook of Polyethylene Structures, Properties, and Applications, pp. 1-5 (Copyright 2000).*
(Continued)

*Primary Examiner* — Fred M Teskin
(74) *Attorney, Agent, or Firm* — Conley Rose, P.C.; Rodney B. Carroll; Monte R. Rhodes

(57) ABSTRACT

A process for recovery of ethylene from a polymerization product stream of a polyethylene production system, comprising separating a light gas stream from the polymerization product stream, wherein the light gas stream comprises ethane and unreacted ethylene, contacting the light gas stream with an absorption solvent system, wherein the contacting the light gas stream with the absorption solvent system occurs at a temperature in a range of from about 40° F. to about 110° F., wherein at least a portion of the unreacted ethylene from the light gas stream is absorbed by the absorption solvent system, and recovering unreacted ethylene from the absorption solvent system to yield recovered ethylene.

30 Claims, 9 Drawing Sheets

Related U.S. Application Data continuation of application No. 13/446,965, filed on Apr. 13, 2012, now Pat. No. 9,180,405, which is a continuation-in-part of application No. 12/905,966, filed on Oct. 15, 2010, now Pat. No. 8,410,329.

(51) Int. Cl.

| | | |
|---|---|---|
| *C07C 5/327* | (2006.01) | |
| *B01J 19/24* | (2006.01) | |
| *B01D 53/18* | (2006.01) | |
| *C08F 6/00* | (2006.01) | |
| *C08F 110/02* | (2006.01) | |
| *C08L 23/04* | (2006.01) | |
| *B01D 53/14* | (2006.01) | |
| *C08F 2/12* | (2006.01) | |
| *C08F 10/02* | (2006.01) | |

(52) U.S. Cl.
CPC .............. *B01D 53/18* (2013.01); *B01J 19/24* (2013.01); *B01J 19/2455* (2013.01); *C07C 5/327* (2013.01); *C08F 6/001* (2013.01); *C08F 110/02* (2013.01); *B01D 2252/10* (2013.01); *B01D 2252/20405* (2013.01); *B01D 2252/20421* (2013.01); *B01D 2252/20431* (2013.01); *B01D 2252/20436* (2013.01); *B01D 2252/20468* (2013.01); *B01D 2252/504* (2013.01); *B01D 2257/7022* (2013.01); *B01J 2219/24* (2013.01); *C08F 10/02* (2013.01)

(58) Field of Classification Search
USPC .......................................................... 526/65
See application file for complete search history.

(56) References Cited

U.S. PATENT DOCUMENTS

| | | | |
|---|---|---|---|
| 3,248,179 | A | 4/1966 | Norwood |
| 3,755,487 | A | 8/1973 | Jahnig et al. |
| 4,025,574 | A | 5/1977 | Tabler et al. |
| 4,501,885 | A | 2/1985 | Sherk et al. |
| 4,588,790 | A | 5/1986 | Jenkins, III et al. |
| 5,104,570 | A | 4/1992 | Cymbaluk et al. |
| 5,191,153 | A | 3/1993 | Cymbaluk et al. |
| 5,259,986 | A | 11/1993 | Cymbaluk et al. |
| 5,352,749 | A | 10/1994 | DeChellis et al. |
| 5,436,304 | A | 7/1995 | Griffin et al. |
| 5,455,314 | A | 10/1995 | Burns et al. |
| 5,523,512 | A | 6/1996 | Cymbaluk et al. |
| 5,565,175 | A | 10/1996 | Hottovy et al. |
| 5,575,979 | A | 11/1996 | Hanson |
| 5,639,935 | A | 6/1997 | Cooper et al. |
| 5,681,908 | A | 10/1997 | Mehra et al. |
| 6,221,982 | B1 | 4/2001 | Debras et al. |
| 6,225,412 | B1 | 5/2001 | Chaffin et al. |
| 6,225,421 | B1 | 5/2001 | Promel et al. |
| 6,239,235 | B1 | 5/2001 | Hottovy et al. |
| 6,262,191 | B1 | 7/2001 | Hottovy et al. |
| 6,291,601 | B1 | 9/2001 | Debras |
| 6,468,329 | B2 | 10/2002 | Cho et al. |
| 6,730,751 | B2 | 5/2004 | Shamshoum et al. |
| 6,833,415 | B2 | 12/2004 | Kendrick et al. |
| 7,034,092 | B2 * | 4/2006 | Marechal ............ B01J 19/1837 526/124.2 |
| 7,163,906 | B2 | 1/2007 | McDaniel et al. |
| 7,619,047 | B2 | 11/2009 | Yang et al. |
| 7,709,585 | B1 | 5/2010 | Buchelli et al. |
| 8,410,329 | B2 | 4/2013 | Hottovy et al. |
| 9,108,147 | B2 | 8/2015 | Kufeld et al. |
| 9,180,405 | B2 | 11/2015 | Hottovy et al. |
| 9,187,383 | B2 | 11/2015 | Kufeld et al. |
| 9,284,430 | B2 | 3/2016 | Kufeld et al. |
| 2006/0094590 | A1 | 5/2006 | McDaniel et al. |
| 2007/0197374 | A1 | 8/2007 | Yang et al. |
| 2009/0004417 | A1 | 1/2009 | Follestad et al. |
| 2010/0029872 | A1 | 2/2010 | Jensen et al. |
| 2010/0041842 | A1 | 2/2010 | Yang et al. |
| 2011/0046323 | A1 | 2/2011 | Van Der Schrick et al. |
| 2011/0152474 | A1 | 6/2011 | Gessner et al. |
| 2016/0023966 | A1 | 1/2016 | Hottovy et al. |
| 2016/0152745 | A1 | 6/2016 | Kufeld et al. |

FOREIGN PATENT DOCUMENTS

| | | |
|---|---|---|
| EP | 2083020 A1 | 7/2009 |
| WO | 2007018506 A1 | 2/2007 |
| WO | 2012051268 A1 | 4/2012 |
| WO | 2013154882 A1 | 10/2013 |
| WO | 2013154907 A2 | 10/2013 |
| WO | 2013154907 A3 | 10/2013 |

OTHER PUBLICATIONS

Chen, Joseph, et al., "A Study of Cu(I)-Ethylene Complexation for Olefin-Paraffin Separation," AIChE Journal, American Institute of Chemical Engineers, vol. 57 No. 3, pp. 630-644, Mar. 2011.
Engineering Data Book, vol. II, Sections 17-26, Tenth Edition, 1987, p. 19-32, Gas Processors Association.
Extractive distillation, Wikipedia, 3 pages, http://en.wikipedia.org/wiki/Extractive_distillation, last viewed Jan. 28, 2011.
File: simple distillation apparatus.svg, Wikipedia, 5 pages, http://en.wikipedia.org/wiki/File:Simple_distillation_apparatus.svg, last viewed Mar. 2, 2010.
Foreign communication from a related counterpart application—International Search Report and Written Opinion, PCT/US2011/055923, Dec. 27, 2011, 12 pages.
Foreign communication from a related counterpart application—International Preliminary Report on Patentability, PCT/US2011/055923, Apr. 16, 2013, 8 pages.
Foreign communication from a related counterpart application—Invitation to Pay Additional Fees, PCT/US2013/035274, Jul. 31, 2013, 8 pages.
Foreign communication from a related counterpart application—International Search Report and Written Opinion, PCT/US2013/035274, Oct. 14, 2013, 19 pages.
Foreign communication from a related counterpart application—International Preliminary Report on Patentability PCT/US2013/035274, Oct. 14, 2014, 14 pages.
Foreign communication from a related counterpart application—International Search Report and Written Opinion, PCT/US2013/035103, Jul. 31, 2013, 13 pages.
Foreign communication from a related counterpart application—International Preliminary Report on Patentability, PCT/US2013/035103, Oct. 14, 2014, 10 pages.
Jacobs, Marc L., et al., "Maximising membranes," Hydrocarbon Engineering, Jun. 2004, reprint, 3 pages.
Jacobs, Marc L., et al., "Monomer recovery in polyolefin plants," Petrochemicals and Gas Processing, 4 pages, Mar. 1999.
Office Action dated Dec. 9, 2015 (34 pages), U.S. Appl. No. 14/877,590, filed Oct. 7, 2015.
Notice of Allowance dated Mar. 29, 2016 (9 pages), U.S. Appl. No. 14/877,590, filed Oct. 7, 2015.
Office Action dated Jun. 7, 2016 (24 pages), U.S. Appl. No. 15/014,885, filed Feb. 3, 2016.
Polyethylene (PE) Production, Marketing Brochure, MTR Membrane Technology & Research, Inc., 2009, 2 pages.
Seine, Travis A., et al., "Absorption Equilibrium and Kinetics for Ethylene—Ethane Separation with a Novel Solvent," Ind. Eng. Chem. Res., 2005, vol. 44, No. 19, pp. 7505-7510, American Chemical Society.
Reine, Travis Allen, "Olefin/Paraffin Separation by Reactive Absorption," Dissertation, Dec. 2004, 268 pages.
Notice of Allowance dated Dec. 1, 2016 (9 pages), U.S. Appl. No. 15/014,885, filed Feb. 3, 2016.

\* cited by examiner

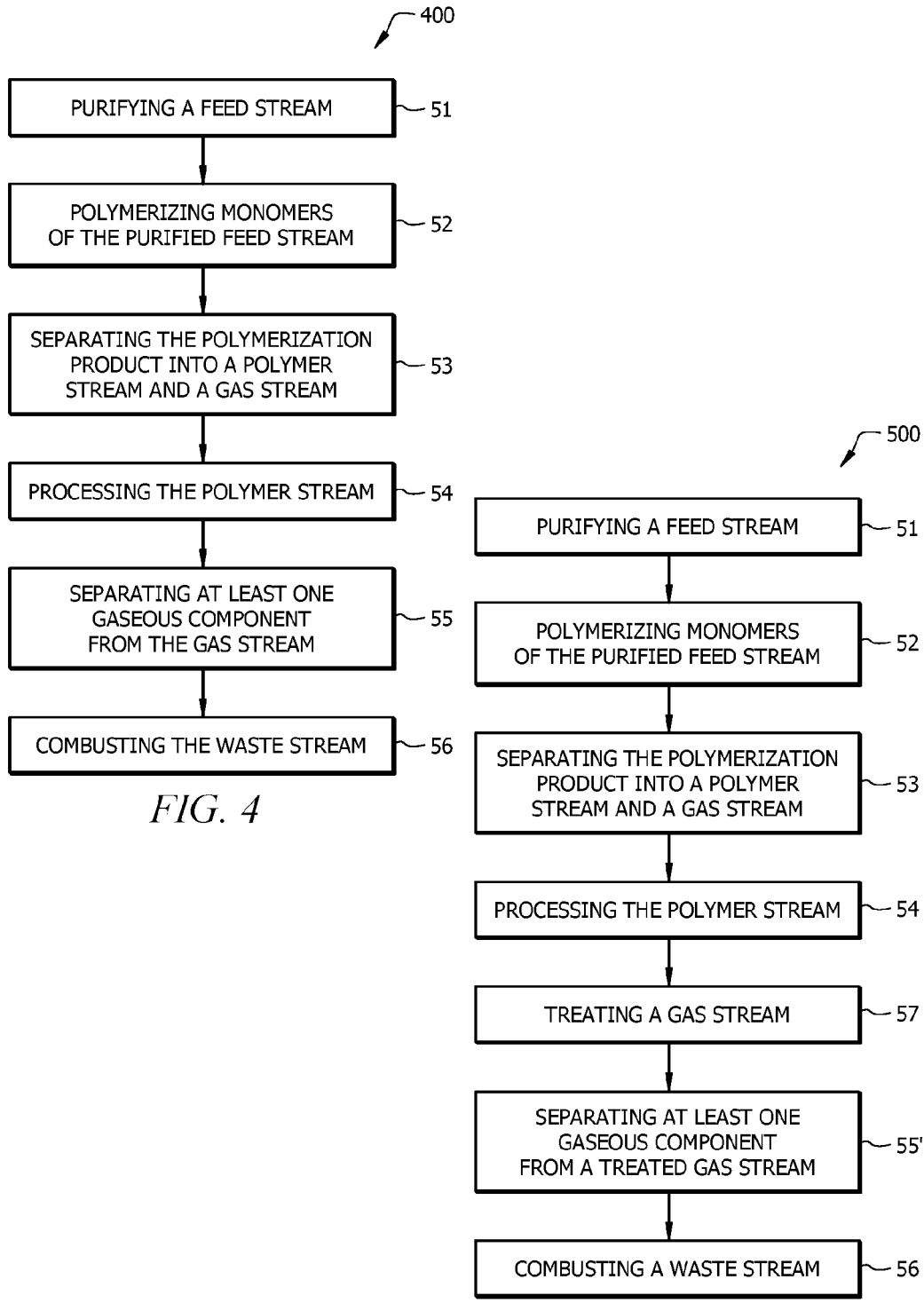

ETHYLENE RECOVERY BY ABSORPTION

CROSS-REFERENCE TO RELATED APPLICATIONS

This application is a continuation of and claims priority to U.S. patent application Ser. No. 14/877,590 filed Oct. 7, 2015, now U.S. Pat. No. 9,399,608 B2 and entitled "Ethylene Recovery by Absorption," which is a continuation of U.S. patent application Ser. No. 13/446,965 filed Apr. 13, 2012, now U.S. Pat. No. 9,180,405 B2 and entitled "Ethylene Recovery by Absorption," which is a continuation-in-part of U.S. patent application Ser. No. 12/905,966, filed Oct. 15, 2010, now U.S. Pat. No. 8,410,329 B2, and entitled "Ethylene Separation," each of which is hereby incorporated herein by reference in its entirety for all purposes.

STATEMENT REGARDING FEDERALLY SPONSORED RESEARCH OR DEVELOPMENT

Not applicable.

BACKGROUND

Field of the Invention

This disclosure generally relates to the production of polyethylene. More specifically this disclosure relates to systems and processes for improving polyethylene production efficiency by decreasing ethylene losses.

Background of the Invention

The production of polymers such as polyethylene from light gases requires a high purity feedstock of monomers and comonomers. Due to the small differences in boiling points between the light gases in such a feedstock, industrial production of a high purity feedstock may require the operation of multiple distillation columns, high pressures, and cryogenic temperatures. As such, the energy costs associated with feedstock purification represent a significant proportion of the total cost for the production of such polymers. Further, the infrastructure required for producing, maintaining, and recycling high purity feedstock is a significant portion of the associated capital cost.

In order to offset some of the costs and maximize production, it can be useful to reclaim and/or recycle any unreacted feedstock gases, especially the light hydrocarbon reactants, such as ethylene. Gases comprising unreacted monomers may be separated from the polymer after the polymerization reaction. The polymer is processed while the unreacted monomers are recovered from the gases that are reclaimed following the polymerization reaction. To accomplish this, the reclaimed gas streams have conventionally either been routed through a purification process or redirected through other redundant processing steps. In either case, conventional processes of recovering monomer have necessitated energetically unfavorable and expensive processes.

Consequently, there is a need for high-efficiency separation of ethylene from a recycle stream.

BRIEF SUMMARY

Disclosed herein is a process for recovery of ethylene from a polymerization product stream of a polyethylene production system, comprising separating a light gas stream from the polymerization product stream, wherein the light gas stream comprises ethane and unreacted ethylene, contacting the light gas stream with an absorption solvent system, wherein the contacting the light gas stream with the absorption solvent system occurs at a temperature in a range of from about 40° F. to about 110° F., wherein at least a portion of the unreacted ethylene from the light gas stream is absorbed by the absorption solvent system, and recovering unreacted ethylene from the absorption solvent system to yield recovered ethylene.

Further disclosed herein is a polyethylene production process, comprising contacting ethylene and a polymerization catalyst in a polymerization reactor under suitable reaction conditions to yield a polymerization product stream, separating a light gas stream from the polymerization product stream, wherein the light gas stream comprises unreacted ethylene, contacting the light gas stream with an absorption solvent system in an absorption reactor at a temperature in a range of from about 40° F. to about 110° F., wherein at least a portion of the unreacted ethylene from the light gas stream is absorbed by the absorption solvent system to yield a composition comprising a complex of the absorption solvent system and unreacted ethylene, removing unabsorbed gases of the light gas stream from contact with the absorption solvent system, recovering unreacted ethylene from the absorption solvent system, and contacting the recovered ethylene and the polymerization catalyst.

Also disclosed herein is a polyethylene production system, comprising a feed stream comprising ethylene, wherein the feed stream is characterized by introduction into a polymerization reactor, a polymerization product stream, wherein the polymerization product stream is characterized by emission from the polymerization reactor and introduction into a separator, a light gas stream comprising unreacted ethylene, wherein the light gas stream is characterized by emission from the separator, the light gas stream having been separated from the polymerization product stream, wherein the light gas stream is characterized by introduction into an absorption solvent system, wherein the absorption solvent system has a temperature in a range of from about 40° F. to about 110° F., an absorbent-ethylene conjugant, wherein the absorbent-ethylene conjugant is characterized by formation within the absorption solvent system by absorption of at least a portion of the unreacted ethylene by the absorption solvent system, and a waste gas stream comprising ethane, wherein the waste gas stream is characterized by emission from the absorption reactor, wherein the waste gas stream comprises components of the light gas stream that are not absorbed by the absorption solvent system, and a recovered unreacted ethylene stream, wherein the recovered unreacted ethylene stream is characterized by emission from the absorption reactor and reintroduction into the polymerization reactor.

Also disclosed herein is a polyethylene production system, comprising a polymerization reactor, wherein the polymerization reactor is configured to receive a feed stream comprising ethylene, and wherein the polymerization reactor is configured to emit a polymerization product stream, a separator, wherein the separator is configured to receive the polymerization product stream and to emit a light gas stream comprising unreacted ethylene, wherein the light gas stream has been separated from the polymerization product stream, and an absorption reactor comprising an absorption solvent system, wherein the absorption reactor is configured to receive the light gas stream, to absorb at least a portion of the unreacted ethylene with the absorption solvent system at a temperature in a range of from about 40° F. to about 110° F., and to emit a waste gas stream comprising components of the light gas stream that are not absorbed by the absorption solvent system, and wherein the absorption reactor is further configured to emit a recovered unreacted ethylene stream, and wherein the polymerization reactor is further configured to receive the recovered unreacted ethylene stream.

Also disclosed herein is a polyethylene production system, comprising a polymerization reactor, wherein the polymerization reactor is configured to receive a feed stream comprising ethylene, and wherein the polymerization reactor is configured to emit a polymerization product stream, a separator, wherein the separator is configured to receive the polymerization product stream and to emit a light gas stream comprising unreacted ethylene, wherein the light gas stream has been separated from the polymerization product stream, an absorption reactor comprising an absorption solvent system, wherein the absorption reactor is configured to receive the light gas stream, to absorb at least a portion of the unreacted ethylene with the absorption solvent system at a temperature in a range of from about 40° F. to about 110° F. and to emit a waste gas stream comprising components of the light gas stream that are not absorbed by the absorption solvent system, wherein the absorption reactor is further configured to emit a complexed stream comprising ethylene absorbed in the absorbent solvent system, and a solvent regenerator to regenerate the absorption solvent system, and to emit a recovered unreacted ethylene stream, wherein the polymerization reactor is further configured to receive the recovered unreacted ethylene stream.

The foregoing has outlined rather broadly the features and technical advantages of the disclosed inventive subject matter in order that the following detailed description may be better understood. The various characteristics described above, as well as other features, will be readily apparent to those skilled in the art upon reading the following detailed description of the preferred embodiments, and by referring to the accompanying drawings.

DESCRIPTION OF THE DRAWINGS

For a detailed description of the preferred embodiments of the disclosed processes and systems, reference will now be made to the accompanying drawings in which:

FIG. 4 illustrates a flow diagram of a first embodiment of a polyethylene production process;

FIG. 5 illustrates a flow diagram of a second embodiment of a polyethylene production process;

DETAILED DESCRIPTION

Disclosed herein are systems, apparatuses, and processes related to the production of polyethylene with improved efficiency. The systems, apparatuses, and processes are generally related to the separation of a first chemical component or compound from a composition resulting from the production of polyethylene and comprising the first chemical component or compound and one or more other chemical components, compounds, or the like.

Figure 1:
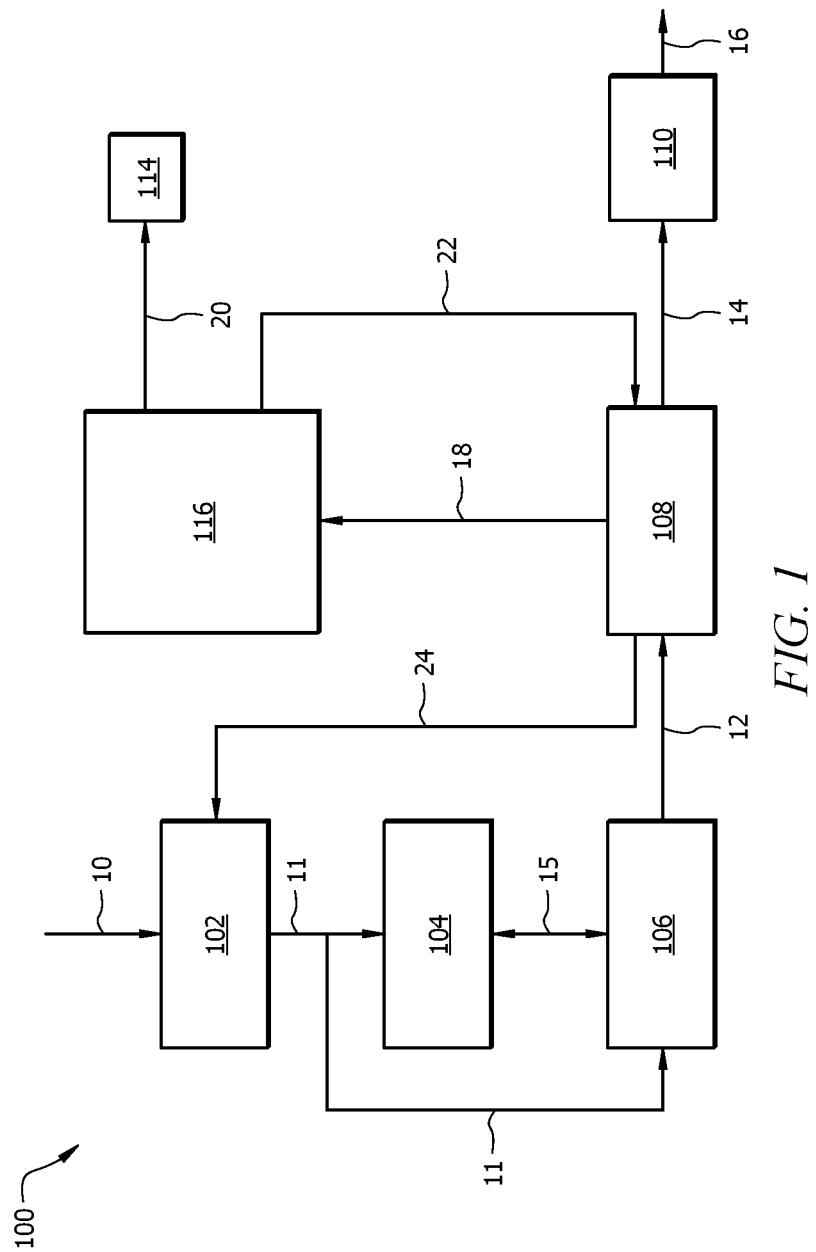
FIG. 1 illustrates a schematic of a first embodiment of a polyethylene production system.

Referring to FIG. 1, a first polyethylene production (PEP) is disclosed. PEP system 100 generally comprises a purifier 102, reactors 104, 106, a separator 108, a processor 110, an absorption reactor 116, and a processing device 114. In the PEP embodiments disclosed herein, various system components may be in fluid communication via one or more conduits (e.g., pipes, tubing, flow lines, etc.) suitable for the conveyance of a particular stream, for example as show in detail by the numbered streams in FIGS. 1-3.

In the embodiment of FIG. 1, a feed stream 10 may be communicated to the purifier 102. A purified feed stream 11 may be communicated from the purifier 102 to one or more of the reactors 104, 106. Where such a system comprises two or more reactors, a reactor stream 15 may be communicated from reactor 104 to reactor 106. A polymerization product stream 12 may be communicated from one or more of the reactors 104, 106 to the separator 108. A polymer stream 14 may be communicated from the separator 108 to the processor 110. A product stream 16 may be emitted from the processor 110. A gas stream 18 may be communicated from the separator 108 to the absorption reactor 116. A waste gas stream 20 may be communicated from the absorption reactor 116 to the processing device 114 and a recycle stream 22 may be communicated from the absorption reactor 116 to the separator 108. A reintroduction stream 24 may be communicated from the separator 108 to the purifier 102.

Figure 2:
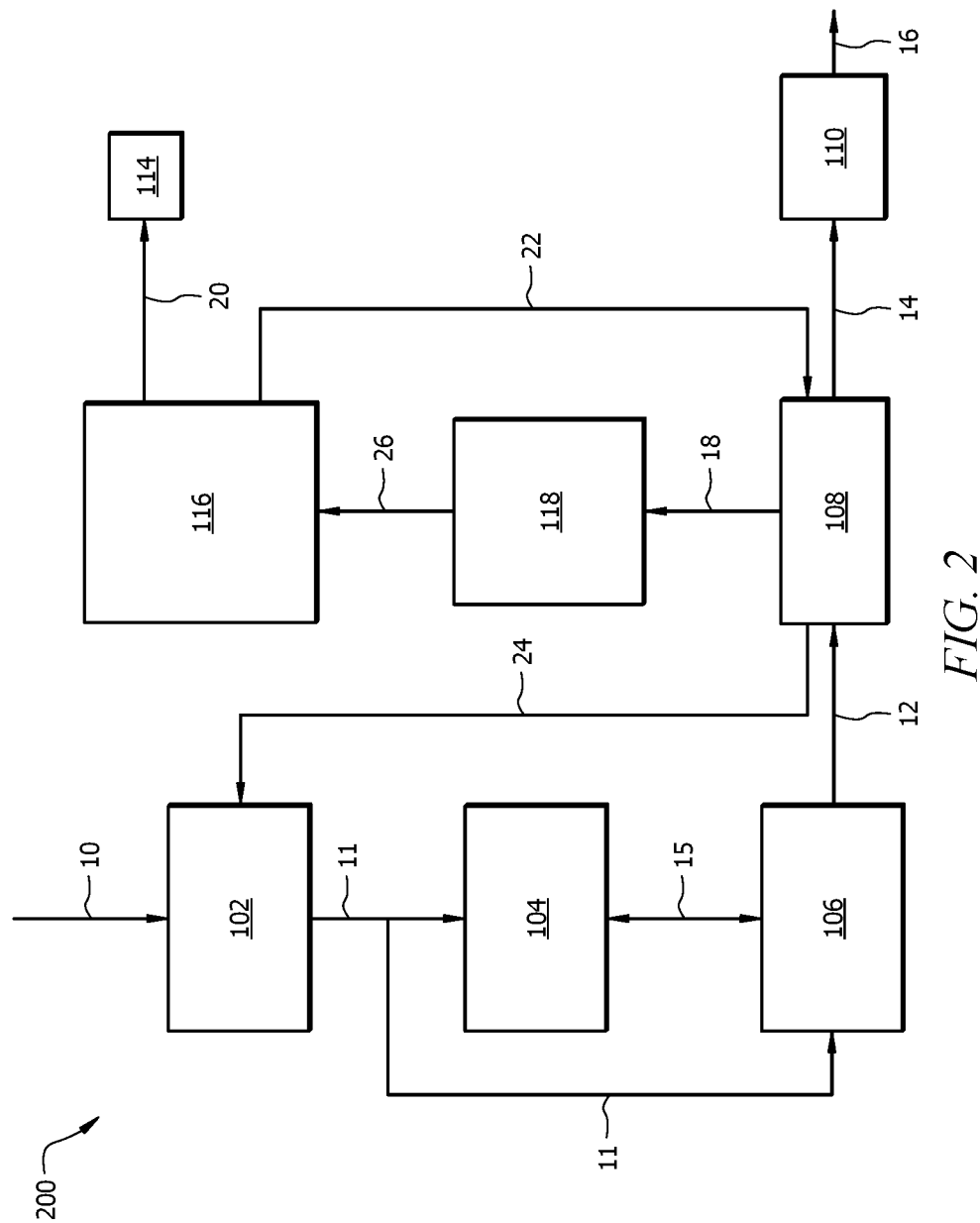
FIG. 2 illustrates a schematic of a second embodiment of a polyethylene production system.

Referring to FIG. 2, a second PEP system 200 is disclosed, which has a number of system components common with PEP 100. In the alternative embodiment illustrated by FIG. 2, the second PEP system 200 additionally comprises a deoxygenator 118. Alternatively to the first PEP system 100 (as illustrated in FIG. 1), in the embodiment illustrated by FIG. 2, the gas stream 18 may be communicated to the deoxygenator 118. A treated gas stream 26 may be communicated from the deoxygenator 118 to the absorption reactor 116.

Figure 3:
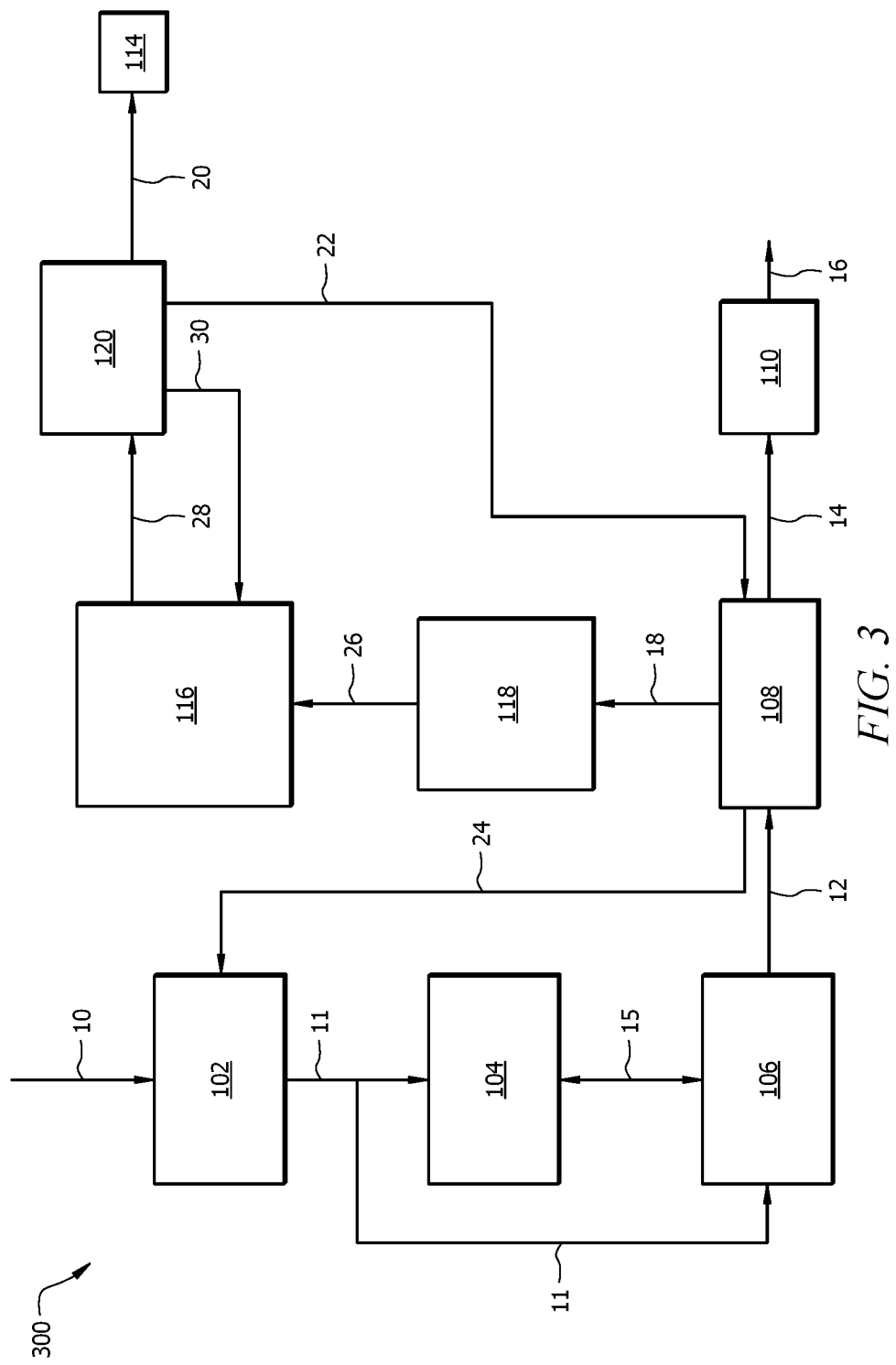
FIG. 3 illustrates a schematic of a third embodiment of a polyethylene production system.

Referring to FIG. 3, a third PEP system 300 is disclosed, which has a number of system components common with PEP 100 and PEP 200. In the alternative embodiment illustrated by FIG. 3, the third PEP system 300 additionally comprises a regenerator 120 (e.g., a desorption vessel). Alternatively to the first and second PEP systems 100 and 200, respectively, in the embodiment illustrated in FIG. 3, a complexed stream 28 may be communicated from the absorption reactor 116 to the regenerator 120. A recycle stream 22 may be communicated from the regenerator 120 to the separator 108, and a regenerated absorbent stream 30 may be communicated from the regenerator 120 to the absorption reactor 116.

In FIG. 3, a temperature of lean solvent may be taken from stream 30. The temperature of the absorption reactor 116 may depend on a temperature of gas stream 18, a temperature of lean solvent in stream 30, a heat of solution, and a heat of reaction. In the disclosed embodiments, the mass flow rate of lean solvent in stream 30 may be 50 to 300 times greater than a mass flow rate of the gas stream 18. Therefore, the temperature of the absorption reactor 116 may highly depend on the temperature of lean solvent in the disclosed embodiments.

Various embodiments of suitable PEP systems having been disclosed, embodiments of a PEP process are now disclosed. One or more of the embodiments of a PEP process may be described with reference to one or more of PEP system 100, PEP system 200, and/or PEP system 300. Although a given PEP process may be described with reference to one or more embodiments of a PEP system, such a disclosure should not be construed as so-limiting. Although the various steps of the processes disclosed herein may be disclosed or illustrated in a particular order, such should not be construed as limiting the performance of these processes to any particular order unless otherwise indicated.

Referring to FIG. 4, a first PEP process 400 is illustrated. PEP process 400 generally comprises at block 51 purifying a feed stream, at block 52 polymerizing monomers of the purified feed stream to form a polymerization product, at block 53 separating the polymerization product into a polymer stream and a gas stream, at block 54 processing the polymer stream, at block 55 separating at least one gaseous component from the gas stream to form a recycle stream and a waste stream, and at block 56 combusting the waste stream.

In an embodiment, the first PEP process 400 or a portion thereof may be implemented via the first PEP system 100 (e.g., as illustrated in FIG. 1). Referring to FIGS. 1 and 4, in an embodiment the feed stream 10 may comprise a gaseous reactant, particularly, ethylene. In an embodiment, purifying the feed stream may yield a purified stream 11 comprising substantially pure monomers (e.g., ethylene monomers), comonomers (e.g., butene-1 comonomers, or combinations thereof. Polymerizing monomers (optionally, comonomers) of the purified stream 11 may yield the polymerization product stream 12 generally comprising unreacted monomer (e.g., ethylene), optional unreacted comonomer (e.g., butene-1), by-products (e.g., ethane, which may be by-product ethane formed from ethylene and hydrogen), and a polymerization product (e.g., polymer and optionally, copolymer). Separating the polymerization product stream 12 may yield the polymer stream 14 (e.g., polyethylene polymer, copolymer) and the gas stream 18 generally comprising unreacted monomer (e.g., ethylene monomer and any optional comonomer such as butene-1) and various waste gases (e.g., ethane). Processing the polymer stream 14 may yield the product stream 16. Separating at least one gaseous component from the gas stream 18 may yield a recycle stream 22, generally comprising unreacted ethylene monomer (optionally, unreacted comonomer), and a waste gas stream 20. In an embodiment, separating the gas stream 18 comprises absorbing ethylene from the gas stream 18 to yield the waste gas stream 20 and then releasing the absorbed ethylene to form the recycle stream 22. The recycle stream 22, comprising ethylene, may be pressurized (e.g., returned to the separator 108 for pressurization) and reintroduced into a PEP process (e.g., PEP process 400) as reintroduction stream 24. Combusting the waste gas stream 20 may be carried out with a flare as the processing device 114.

Referring to FIG. 5, a second PEP process 500 is illustrated, which has a number of process steps common with PEP process 400. In the alternative embodiment illustrated by FIG. 5, block 55 of FIG. 4 is enhanced by at block 57 treating the gas stream to form a treated gas stream and at block 55' separating at least one gaseous component from the treated gas stream to form a recycle stream and a waste stream.

In an embodiment, second PEP process 500 or a portion thereof may be implemented via the second PEP system 200 (e.g. as illustrated in FIG. 2). Alternatively to the embodiments of FIGS. 1 and 4, in the embodiment of FIGS. 2 and 5 treating the gas stream 18 may yield the treated gas stream 26. In an embodiment, treating the gas stream 18 comprises deoxygenating the gas stream 18. Separating at least one gaseous component from the treated gas stream 26 may yield a recycle stream 22, generally comprising unreacted ethylene monomer (optionally, comonomer), and a waste gas stream 20.

Figure 6:
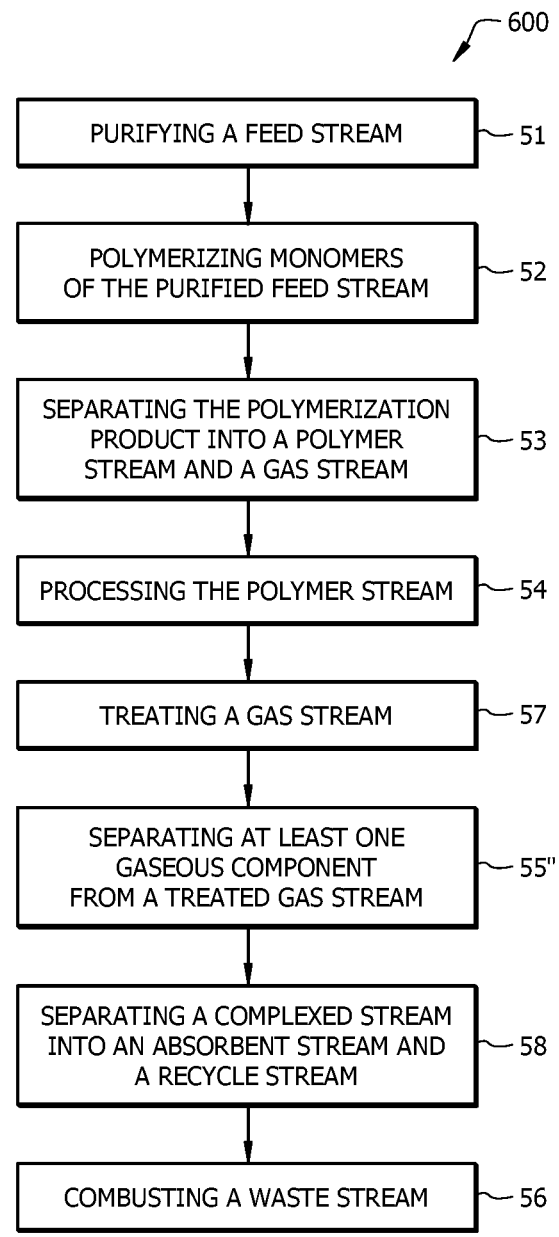
FIG. 6 illustrates a flow diagram of a third embodiment of a polyethylene production process.

Referring to FIG. 6, a third PEP process 600 is illustrated, which has a number of process steps common with PEP process 500. In the alternative embodiment illustrated by FIG. 6, block 55' of FIG. 5 is enhanced by at block 55" separating at least one gaseous component from the treated gas stream to form a complexed stream and a waste gas stream and at block 58 separating the complexed stream into an absorbent stream and a recycle stream.

In an embodiment, third PEP process 600 or a portion thereof may be implemented via the third PEP system 300 (e.g. as illustrated in FIG. 3). Alternatively to the embodiments of FIGS. 1&4 and 2&5, in the embodiment of FIGS. 3 and 6 separating at least one gaseous component from the treated gas stream 26 may yield an unreacted monomer-absorbent (e.g., an ethylene-absorbent) in complexed stream 28. In an embodiment, separating the unreacted monomer-absorbent complexed stream 28 comprises releasing the absorbed ethylene to form a recycle stream 22 and a regenerated absorbent stream 30. In the embodiment of FIGS. 3 and 6, separating at least one gaseous component from the treated gas stream 26 may yield an unreacted comonomer-absorbent (e.g., a butene-1-absorbent) in complexed stream 28. In an embodiment, separating the unreacted comonomer-absorbent in complexed stream 28 comprises releasing the absorbed comonomer to form a recycle stream 22 and a regenerated absorbent stream 30.

In one or more of the embodiments disclosed herein, purifying a feed stream (e.g., at block 51) may comprise separating unwanted compounds and elements from a feed stream comprising ethylene to form a purified feed stream. In an embodiment, the feed stream may comprise ethylene and various other gases, such as but not limited to methane, ethane, acetylene, propylene, various other hydrocarbons having three or more carbon atoms, or combinations thereof. In an embodiment, purifying a feed stream may comprise any suitable method or process, including the non-limiting examples filtering, membrane screening, reacting with various chemicals, absorbing, adsorbing, distillation(s), or combinations thereof.

In embodiments as illustrated by FIGS. 1-3, purifying a feed stream may comprise routing the feed stream 10 to the purifier 102. In one or more of the embodiments disclosed herein, the purifier 102 may comprise a device or apparatus suitable for the purification of one or more reactant gases in a feed stream comprising a plurality of potentially unwanted gaseous compounds, elements, contaminants, or the like. Non-limiting examples of a suitable purifier 102 may comprise a filter, a membrane, a reactor, an absorbent, a molecular sieve, one or more distillation columns, or combinations thereof. The purifier 102 may be configured to separate ethylene from a stream comprising methane, ethane, acetylene, propane, propylene, water, oxygen various other gaseous hydrocarbons, various contaminants, and/or combinations thereof.

In an embodiment, purifying a feed stream may yield a purified feed 11 comprising substantially pure ethylene. In an embodiment, the purified feed stream may comprise less than 25% by total weight of the stream, alternatively, less than about 10%, alternatively, less than about 1.0% of any one or more of nitrogen, oxygen, methane, ethane, propane, or combinations thereof. As used herein "substantially pure ethylene" refers to a fluid stream comprising at least about 60% ethylene, alternatively, at least about 70% ethylene, alternatively, at least about 80% ethylene, alternatively, at least about 90% ethylene, alternatively, at least about 95% ethylene, alternatively, at least about 99% ethylene by total weight of the stream, alternatively, at least about 99.5% ethylene by total weight of the stream. In an embodiment, the feed stream 11 may further comprise trace amounts of ethane, for example, as from a recycle stream as will be discussed.

In one or more of the embodiments disclosed herein, polymerizing monomers of the purified feed (e.g., at block 52) may comprise allowing a polymerization reaction between a plurality of monomers by contacting a monomer or monomers with a catalyst system under conditions suitable for the formation of a polymer. In one or more of the embodiments disclosed herein, polymerizing comonomers (e.g., at block 52) may comprise allowing a polymerization reaction between a plurality of comonomers by contacting a comonomer or comonomers with a catalyst system under conditions suitable for the formation of a copolymer. In an embodiment, any suitable catalyst system may be employed. A suitable catalyst system may comprise a catalyst and, optionally, a co-catalyst and/or promoter. Nonlimiting examples of suitable catalyst systems include Ziegler Natta catalysts, Ziegler catalysts, chromium catalysts, chromium oxide catalysts, chromocene catalysts, metallocene catalysts, nickel catalysts, or combinations thereof. Catalyst systems suitable for use in this disclosure have been described, for example, in U.S. Pat. No. 7,619,047 and U.S. Patent Application Publication Nos. 2007/0197374, 2009/0004417, 2010/0029872, 2006/0094590, and 2010/0041842, each of which is incorporated by reference herein in its entirety.

In embodiments as illustrated by FIGS. 1-3, polymerizing monomers of the purified feed may comprise routing the feed stream 11 to the polymerization reactors or "reactors" 104, 106. In one or more of the embodiments disclosed herein, the reactors 104, 106 may comprise any vessel or combination of vessels suitably configured to provide an environment for a chemical reaction (e.g., a contact zone) between monomers (e.g., ethylene) and/or polymers (e.g., an "active" or growing polymer chain), and optionally comonomers (e.g., butene-1) and/or copolymers, in the presence of a catalyst to yield a polymer (e.g., a polyethylene polymer) and/or copolymer. Although the embodiments illustrated in FIGS. 1, 2, and 3, illustrate various PEP systems having two reactors in series, one of skill in the art viewing this disclosure will recognize that one reactor, alternatively, any suitable number and/or configuration of reactors may be employed.

As used herein, the terms "polymerization reactor" or "reactor" include any polymerization reactor capable of polymerizing olefin monomers or comonomers to produce homopolymers or copolymers. Such homopolymers and copolymers are referred to as resins or polymers. The various types of reactors include those that may be referred to as batch, slurry, gas-phase, solution, high pressure, tubular or autoclave reactors. Gas phase reactors may comprise fluidized bed reactors or staged horizontal reactors. Slurry reactors may comprise vertical or horizontal loops. High pressure reactors may comprise autoclave or tubular reactors. Reactor types can include batch or continuous processes. Continuous processes could use intermittent or continuous product discharge. Processes may also include partial or full direct recycle of unreacted monomer, unreacted comonomer, and/or diluent.

Polymerization reactor systems of the present disclosure may comprise one type of reactor in a system or multiple reactors of the same or different type. Production of polymers in multiple reactors may include several stages in at least two separate polymerization reactors interconnected by a transfer device making it possible to transfer the polymers resulting from the first polymerization reactor (e.g., reactor 104) into the second reactor (e.g., reactor 106). The desired polymerization conditions in one of the reactors may be different from the operating conditions of the other reactors. Alternatively, polymerization in multiple reactors may include the manual transfer of polymer from one reactor to subsequent reactors for continued polymerization. Multiple reactor systems may include any combination including, but not limited to, multiple loop reactors, multiple gas reactors, a combination of loop and gas reactors, multiple high pressure reactors or a combination of high pressure with loop and/or gas reactors. The multiple reactors may be operated in series or in parallel.

According to one aspect, the polymerization reactor system may comprise at least one loop slurry reactor comprising vertical or horizontal loops. Monomer, diluent, catalyst, and optionally any comonomer, may be continuously fed to a loop reactor where polymerization occurs. Generally, continuous processes may comprise the continuous introduction of a monomer, an optional comonomer, a catalyst, and a diluent into a polymerization reactor and the continuous removal from this reactor of a suspension comprising polymer particles and the diluent. Reactor effluent may be flashed to remove the solid polymer from the liquids that comprise the diluent, monomer and/or comonomer. Various technologies may be used for this separation step including but not limited to, flashing that may include any combination of heat addition and pressure reduction; separation by cyclonic action in either a cyclone or hydrocyclone; or separation by centrifugation.

In one or more embodiments, a comonomer may comprise unsaturated hydrocarbons having 3 to 12 carbon atoms. For example, a comonomer may comprise propene, butene-1, hexene-1, octenes, or combinations thereof.

A typical slurry polymerization process (also known as the particle form process), is disclosed, for example, in U.S. Pat. Nos. 3,248,179, 4,501,885, 5,565,175, 5,575,979, 6,239,235, 6,262,191 and 6,833,415, each of which is incorporated by reference in its entirety herein.

In embodiments, suitable diluents used in slurry polymerization include, but are not limited to, the monomer, and optionally, the comonomer, being polymerized and hydrocarbons that are liquids under reaction conditions. Examples of suitable monomer diluents include, but are not limited to, hydrocarbons such as propane, cyclohexane, isobutane, n-butane, n-pentane, isopentane, neopentane, and n-hexane. In embodiments, comonomer diluents may comprise unsaturated hydrocarbons having 3 to 12 carbon atoms. Examples of suitable comonomer diluents include, but are not limited to propene, butene-1, hexene-1, octenes, or combinations thereof. Some loop polymerization reactions can occur under bulk conditions where no diluent is used. An example is polymerization of propylene monomer as disclosed in U.S. Pat. No. 5,455,314, which is incorporated by reference herein in its entirety.

According to yet another aspect, the polymerization reactor may comprise at least one gas phase reactor. Such systems may employ a continuous recycle stream containing one or more monomers continuously cycled through a fluidized bed in the presence of the catalyst under polymerization conditions. A recycle stream may be withdrawn from the fluidized bed and recycled back into the reactor. Simultaneously, polymer product may be withdrawn from the reactor and new or fresh monomer may be added to replace the polymerized monomer. Likewise, copolymer product may optionally be withdrawn from the reactor and new or fresh comonomer may be added to replace polymerized comonomer, polymerized monomer, or combinations thereof. Such gas phase reactors may comprise a process for multi-step gas-phase polymerization of olefins, in which olefins are polymerized in the gaseous phase in at least two independent gas-phase polymerization zones while feeding a catalyst-containing polymer formed in a first polymerization zone to a second polymerization zone. One type of gas phase reactor is disclosed in U.S. Pat. Nos. 5,352,749, 4,588,790 and 5,436,304, each of which is incorporated by reference in its entirety herein.

According to still another aspect, a high pressure polymerization reactor may comprise a tubular reactor or an autoclave reactor. Tubular reactors may have several zones where fresh monomer (optionally, comonomer), initiators, or catalysts may be added. Monomer (optionally, comonomer) may be entrained in an inert gaseous stream and introduced at one zone of the reactor. Initiators, catalysts, and/or catalyst components may be entrained in a gaseous stream and introduced at another zone of the reactor. The gas streams may be intermixed for polymerization. Heat and pressure may be employed appropriately to obtain optimal polymerization reaction conditions.

According to yet another aspect, the polymerization reactor may comprise a solution polymerization reactor wherein the monomer (optionally, comonomer) may be contacted with the catalyst composition by suitable stirring or other means. A carrier comprising an inert organic diluent or excess monomer (optionally, comonomer) may be employed. If desired, the monomer and/or optional comonomer may be brought in the vapor phase into contact with the catalytic reaction product, in the presence or absence of liquid material. The polymerization zone is maintained at temperatures and pressures that will result in the formation of a solution of the polymer in a reaction medium. Agitation may be employed to obtain better temperature control and to maintain uniform polymerization mixtures throughout the polymerization zone. Adequate means are utilized for dissipating the exothermic heat of polymerization.

Polymerization reactors suitable for the disclosed systems and processes may further comprise any combination of at least one raw material feed system, at least one feed system for catalyst or catalyst components, and/or at least one polymer recovery system. Suitable reactor systems may further comprise systems for feedstock purification, catalyst storage and preparation, extrusion, reactor cooling, polymer recovery, fractionation, recycle, storage, loadout, laboratory analysis, and process control.

Conditions that are controlled for polymerization efficiency and to provide resin properties include temperature, pressure and the concentrations of various reactants. Polymerization temperature can affect catalyst productivity, polymer molecular weight and molecular weight distribution. Suitable polymerization temperature may be any temperature below the de-polymerization temperature according to the Gibbs Free energy equation. Typically this includes from about 60° C. to about 280° C., for example, and from about 70° C. to about 110° C., depending upon the type of polymerization reactor.

Suitable pressures will also vary according to the reactor and polymerization type. The pressure for liquid phase polymerizations in a loop reactor is typically less than 1000 psig. Pressure for gas phase polymerization is usually at about 200 to 500 psig. High pressure polymerization in tubular or autoclave reactors is generally run at about 20,000 to 75,000 psig. Polymerization reactors can also be operated in a supercritical region occurring at generally higher temperatures and pressures. Operation above the critical point of a pressure/temperature diagram (supercritical phase) may offer advantages. In an embodiment, polymerization may occur in an environment having a suitable combination of temperature and pressure. For example, polymerization may occur at a pressure in a range from about 550 psi to about 650 psi, alternatively, about 600 psi to about 625 psi and a temperature in a range from about 170° F. to about 230° F., alternatively, from about 195° F. to about 220° F.

The concentration of various reactants can be controlled to produce resins with certain physical and mechanical properties. The proposed end-use product that will be formed by the resin and the method of forming that product determines the desired resin properties. Mechanical properties include tensile, flexural, impact, creep, stress relaxation and hardness tests. Physical properties include density, molecular weight, molecular weight distribution, melting temperature, glass transition temperature, temperature melt of crystallization, density, stereoregularity, crack growth, long chain branching and rheological measurements.

The concentrations and/or partial pressures of monomer, comonomer, hydrogen, co-catalyst, modifiers, and electron donors are important in producing these resin properties. Comonomer may be used to control product density. Hydrogen may be used to control product molecular weight. Cocatalysts can be used to alkylate, scavenge poisons and control molecular weight. Modifiers can be used to control product properties and electron donors affect stereoregularity, the molecular weight distribution, or molecular weight. In addition, the concentration of poisons is minimized because poisons impact the reactions and product properties.

In an embodiment, polymerizing monomers of the purified feed may comprise introducing a suitable catalyst system into the first and/or second reactor 104, 106, respectively, so as to form a slurry. Alternatively, a suitable catalyst system may reside in the first and/or second reactor 104, 106, respectively.

As explained above, polymerizing monomers of the purified feed may comprise selectively manipulating one or more polymerization reaction conditions to yield a given polymer product, to yield a polymer product having one or more desirable properties, to achieve a desired efficiency, to achieve a desired yield, the like, or combinations thereof. Non-limiting examples of such parameters include temperature, pressure, type and/or quantity of catalyst or co-catalyst, and the concentrations and/or partial pressures of various reactants. In an embodiment, polymerizing monomers of the purified feed 52 may comprise adjusting one or more polymerization reaction conditions.

In an embodiment, polymerizing monomers of the purified feed may comprise maintaining a suitable temperature, pressure, and/or partial pressure(s) during the polymerization reaction, alternatively, cycling between a series of suitable temperatures, pressures, and/or partials pressure(s) during the polymerization reaction.

In an embodiment, polymerizing monomers of the purified feed may comprise circulating, flowing, cycling, mixing, agitating, or combinations thereof, the monomers (optionally, comonomers), catalyst system, and/or the slurry within and/or between the reactors 104, 106. In an embodiment where the monomers (optionally, comonomers), catalyst system, and/or slurry are circulated, circulation may be at a velocity (e.g., slurry velocity) of from about 1 m/s to about 30 m/s, alternatively, from about 2 m/s to about 17 m/s, alternatively, from about 3 m/s to about 15 m/s.

In an embodiment, polymerizing monomers of the purified feed may comprise configuring reactors 104, 106 to yield a multimodal (e.g., a bimodal) polymer (e.g., polyethylene). For example, the resultant polymer may comprise both a relatively high molecular weight, low density (HMWLD) polyethylene polymer and a relatively low molecular weight, high density (LMWHD) polyethylene polymer. For example, various types of suitable polymers may be characterized as having a various densities. For example, a Type I may be characterized as having a density in a range of from about 0.910 g/cm$^3$ to about 0.925 g/cm$^3$, alternatively, a Type II may be characterized as having a density from about 0.926 g/cm$^3$ to about 0.940 g/cm$^3$, alternatively, a Type III may be characterized as having a density from about 0.941 g/cm$^3$ to about 0.959 g/cm$^3$, alternatively, a Type IV may be characterized as having a density of greater than about 0.960 g/cm$^3$.

In an embodiment, polymerizing monomers may comprise polymerizing comonomers in one or more of polymerization reactors 104, 106.

In the embodiments illustrated in FIGS. 1-3, polymerizing monomers of the purified feed may yield a polymerization product stream 12. Such a polymerization product stream 12 may generally comprise various solids, semi-solids, volatile and nonvolatile liquids, gases and combinations thereof. In an embodiment, the polymerization product stream 12 may comprise hydrogen, nitrogen, methane, ethylene, ethane, propylene, propane, butane, isobutane, pentane, hexane, hexene-1 and heavier hydrocarbons. In an embodiment, ethylene may be present in a range of from about 0.1% to about 15%, alternatively, from about 1.5% to about 5%, alternatively, about 2% to about 4% by total weight of the stream. Ethane may be present in a range of from about 0.001% to about 4%, alternatively, from about 0.2% to about 0.5% by total weight of the stream. Isobutane may be present in a range from about 80% to about 98%, alternatively, from about 92% to about 96%, alternatively, about 95% by total weight of the stream.

The solids and/or liquids may comprise a polymer product (e.g., a polyethylene polymer), often referred to at this stage of the PEP process as "polymer fluff." The gases may comprise unreacted, gaseous reactant monomers or optional comonomers (e.g., unreacted ethylene monomers, unreacted butene-1 monomers), gaseous waste products, gaseous contaminants, or combinations thereof.

In one or more of the embodiments disclosed herein, separating the polymerization product into a polymer stream and a gas stream (e.g., at block 53) may generally comprise removing any gases from liquids and/or solids (e.g., the polymer fluff) by any suitable process.

In embodiments as illustrated by FIGS. 1-3, separating the polymerization product into a polymer stream and a gas stream may comprise routing the polymerization product steam 12 to the separator 108. In one or more of the embodiments disclosed herein, the separator 108 may be configured to separate a stream (e.g., polymerization product comprising polyethylene) into gases, liquids, solids, or combinations thereof. The reaction product may comprise unreacted, gaseous monomers or optional comonomers (e.g., unreacted ethylene monomers, unreacted butene-1 monomers), gaseous waste products, and/or gaseous contaminants. As used herein, an "unreacted monomer," for example, ethylene, refers to a monomer that was introduced into a polymerization reactor during a polymerization reaction but was not incorporated into a polymer. As used herein, an "unreacted comonomer," for example, butene-1, refers to a comonomer that was introduced into a polymerization reactor during a polymerization reaction but was not incorporated into a polymer.

In an embodiment, the separator 108 may comprise a vapor-liquid separator. Suitable examples of such a separator may include a distillation column, a flash tank, a filter, a membrane, a reactor, an absorbent, an adsorbent, a molecular sieve, or combinations thereof. In an embodiment, the separator comprises a flash tank. Not seeking to be bound by theory, such a flash tank may comprise a vessel configured to vaporize and/or remove low vapor pressure components from a high temperature and/or high pressure fluid. The separator 108 may be configured such that an incoming stream may be separated into a liquid stream (e.g., a condensate stream) and a gas (e.g., vapor) stream. The liquid or condensate stream may comprise a reaction product (e.g., polyethylene, often referred to as "polymer fluff"). The gas or vapor stream may comprise volatile solvents, gaseous, unreacted monomers and/or optional comonomers, waste gases (secondary reaction products, such as contaminants and the like), or combinations thereof. The separator may be configured such that the feed stream is flashed by heat, pressure reduction, or both such that the enthalpy of the stream is increased. This may be accomplished via a heater, a flashline heater, various other operations commonly known in the art, or combinations thereof. For example, a flash line heater comprising a double pipe may exchange heat by hot water or steam. Such a flashline heater may increase the temperature of the stream while reducing its pressure.

In an embodiment, separating the polymerization product into a polymer stream and a gas stream may comprise distilling, vaporizing, flashing, filtering, membrane screening, absorbing, adsorbing, or combinations thereof, the polymerization product. In the embodiments illustrated in FIGS. 1-3, separating the polymerization product into a polymer stream and a gas stream yields a gas stream 18 and a polymer stream 14. In an embodiment, the gas stream 18 may comprise hydrogen, nitrogen, methane, ethylene, ethane, propylene, propane, butane, isobutane, pentane, hexane, hexene-1 and heavier hydrocarbons. In an embodiment, ethylene may be present in a range of from about 0.1% to about 15%, alternatively, from about 1.5% to about 5%, alternatively, about 2% to about 4% by total weight of the stream. Ethane may be present in a range of from about 0.001% to about 4%, alternatively, from about 0.2% to about 0.5% by total weight of the stream. Isobutane may be present in a range from about 80% to about 98%, alternatively, from about 92% to about 96%, alternatively, about 95% by total weight of the stream.

In one or more one or more of the embodiments disclosed herein, processing the polymer stream (e.g., at block 54) comprises any suitable process or series of processes configured to produce a polymer product as may be suitable for commercial or industrial usage, storage, transportation, further processing, or combinations thereof.

In embodiments as illustrated by FIGS. 1-3, processing the polymer stream may comprise routing the polymer stream 14 to the processor 110. The processor 110 may be configured for the performance of a suitable processing means, nonlimiting examples of which include cooling, injection molding, melting, pelletizing, blow molding, extrusion molding, rotational molding, thermoforming, cast molding, the like, or combinations thereof. Various additives and modifiers may be added to the polymer to provide better processing during manufacturing and for desired properties in the end product. Nonlimiting examples of such additives may include surface modifiers such as slip agents, antiblocks, tackifiers; antioxidants such as primary and secondary antioxidants; pigments; processing aids such as waxes/oils and fluoroelastomers; and special additives such as fire retardants, antistats, scavengers, absorbers, odor enhancers, and degradation agents.

In an embodiment, the processor 110 may be configured to form a suitable polymer product. Nonlimiting examples of suitable polymer products as may result from such processing include films, powders, pellets, resins, liquids, or any other suitable form as will be appreciated by those of skill in the art. Such a suitable output may be for use in, for examples, one or more of various consumer or industrial products. For example, the polymer product may be utilized any one or more of various articles, including, but not limited to, bottles, drums, toys, household containers, utensils, film products, drums, fuel tanks, pipes, geomembranes, and liners. In a particular embodiment, the processor is configured to form pellets for transportation to a consumer product manufacturer. For example, in the embodiments illustrated in FIGS. 1-3, processing the polymer stream yields a polymer product 16 (e.g., pelletized polyethylene).

In one or more one or more of the embodiments disclosed herein, treating the gas stream (e.g., at block 57) comprises any suitable process or reaction for removing oxygen, oxygenated compounds, oxidizing compounds, or combinations thereof (cumulatively referred to herein as "oxygen") from the gas stream. Suitable processes or reactions will be appreciated by those of skill in the art viewing this disclosure. Nonlimiting examples of suitable processes for removing oxygen include various catalyzed reactions, contacting with a chemical species known to react with oxygen, filtering, absorbing, adsorbing, heating, cooling, or combinations thereof.

In embodiments as illustrated by FIGS. 2-3, treating the gas stream may comprise routing the gas stream 18 to the deoxygenator 118. In one or more one or more of the embodiments disclosed herein, the deoxygenator 118 may comprise a device or apparatus configured for the removal oxygen, from a gas stream. Nonlimiting examples of a suitable deoxygenator include various reactors (e.g., a fluidized bed reactor or a fixed bed), a filter, or combinations thereof. A suitable deoxygenator 118 may be configured to reduce, prevent, or exclude compounds and/or elements (e.g., oxygen) that may have the effect of poisoning an absorption solvent from reaching the absorption reactor (e.g., as will be disclosed herein).

In the embodiments illustrated by FIGS. 2-3, treating the gas stream yields a treated gas stream 26 being substantially free of oxygen. As used herein "substantially free of oxygen" refers to a fluid stream comprising no more than least about 5% oxygen, alternatively, no more than about 1% oxygen, alternatively, no more than about 0.1% oxygen, alternatively, no more than about 0.01% oxygen by total weight of the stream.

In one or more one or more of the embodiments disclosed herein, separating at least one gaseous component from the gas stream and/or the treated gas stream, collectively referred to as a gas stream, (e.g., at block 55, 55', or 55") generally comprises any suitable method of selectively separating at least a first chemical component or compound from a stream comprising the first chemical component or compound and one or more other chemical components, compounds, or the like. In various embodiments, the gaseous component separated from the gas stream may comprise one or more hydrocarbons. Nonlimiting examples of such hydrocarbons include alkanes (e.g., butane, particularly, isobutane) and alkenes or olefin monomers (e.g., ethylene) or optional comonomers (e.g., butene-1). In an embodiment, the gaseous component separated from the gas stream may comprise an unreacted hydrocarbon monomer, e.g., ethylene. Optionally, the gaseous component separated from the gas stream may comprise an unreacted hydrocarbon comonomer, e.g., propene. In an embodiment, the gaseous component separated from the gas stream may comprise an unreacted hydrocarbon monomer (e.g., ethylene, alone or in combination with other hydrocarbons, such as, isobutane), or optionally, hydrocarbon comonomer (e.g., propene, alone or in combination with other hydrocarbons, such as, isobutane). In an embodiment, the gaseous component separated from the gas stream may comprise ethylene, alone or in combination with isobutane. In an embodiment, capturing isobutane may result in a savings of the cost of the captured isobutane and reduce the presence of isobutane in flare emissions. Nonlimiting examples of suitable separating means include distilling, vaporizing, flashing, filtering, membrane screening, absorbing, adsorbing, molecular weight exclusion, size exclusion, polarity-based separation, or combinations thereof.

In an embodiment, separating at least one gaseous component from the gas stream may comprise contacting the gas stream with the absorbent (e.g., an absorption solvent system, as will be disclosed herein), for example, so as to allow the gaseous component to be absorbent by the absorbent. In such an embodiment, separating at least one gaseous component from the gas stream comprises selectively absorbing the at least one gaseous component from a gas stream. In such an embodiment, absorbing the at least one gaseous component from the gas stream generally comprises contacting the gas stream with a suitable absorbent, allowing the at least one component to be absorbed by the absorbent, and, optionally, removing a waste stream comprising unabsorbed gases. In an additional embodiment, separating at least one gaseous component from the gas stream may further comprise liberating the absorbed gaseous component from the absorbent.

In an embodiment, contacting the gas stream with the absorbent may comprise any suitable means of ensuring sufficient contact between the gas stream and the absorbent. Nonlimiting examples of suitable means by which to provide sufficient contact between the gas stream and the absorbent include the use of various reactor systems, such as those disclosed above (e.g., an absorption column or sparged or mixed tank). Not intending to limited by theory, a suitable reactor system may ensure contact between a two or more gaseous, liquid, and or solid compositions by agitating or mixing the two components in the presence of each other, circulating, dispersing, or diffusing a first composition through or within a second composition, or various other techniques known to those of skill in the art. In an embodiment, the gas stream and the absorbent may be brought into contact in a suitable ratio. Such a suitable ratio of gas stream to absorbent may be in a range of from about 1,000 lb/hr:1000 gpm to about 2,500 lb/hr:25 gpm, alternatively, from about 1000 lb/hr:250 gpm to about 2500 lb/hr:100 gpm, alternatively, about 1875 lb/hr:250 gpm.

In an embodiment as illustrated by FIGS. 1-3, separating at least one gaseous component from the gas stream (e.g., gas stream 18 of FIG. 1 or treated gas stream 26 of FIGS.

2-3) may comprise routing the gas stream to the absorption reactor 116. In one or more of the embodiments disclosed herein, the absorption reactor 116 may comprise a reactor configured to selectively absorb at least a first chemical component or compound from a stream comprising the first chemical component or compound and one or more other chemical components, compounds, or the like. Non-limiting examples of suitable absorption reactors and/or absorption reactor configurations include an absorption (distillation) tower, a pressure-swing absorption (PSA) configuration, a sparger tank, an agitation reactor, one or more compressors, one or more recycle pumps, or combinations thereof.

In an embodiment, the absorption reactor may be configured to dissipate a gas within a liquid (e.g., by bubbling the gas through the liquid). For example, in an embodiment, the absorption reactor 116 may include a solvent circulation system configured to circulate solvent through the absorption reactor 116. The solvent circulation flow rate may be determined by the operating conditions of the absorption system, as is disclosed herein below. In an embodiment, the absorption reactor 116 may comprise and/or be in fluid communication with one or more pumps configured to recirculate solvent via and/or within the absorption reactor 116. In an additional and/or alternative embodiment, the absorption reactor 116 may comprise a packed bed or column configured to maintain smaller bubble sizes (e.g., of the gas being dissipated within the liquid), for example, so as to maintain a relatively large surface area of contact between the gas and the liquid, for example, so as to maintain an efficiency of mass transfer and/or absorption of the gas into the liquid. In an embodiment, the packing material of the packed bed or column may comprise a polymeric material, metallic material, or combinations thereof. In an embodiment, the absorption reactor 116 may have multiple packed beds or columns. In an embodiment, only a section of the absorption reactor 116 may have a packing material. In an embodiment, the packing material of a packed absorption reactor 116 may have a random packing or may have a structured packing. An example of a suitable absorption reactor is illustrated in the Gas Processors Association, "Engineering Data Book" $10^{th}$ ed. at FIG. 19-16.

In an embodiment where the absorption reactor 116 comprises a solvent reactor, the absorption reactor may comprise a suitable absorption solvent system, as will be disclosed herein. Such an absorption reactor 116 may be configured to retain the absorption solvent system. For example, the absorption solvent system may be retained within the reactor as a liquid, as a fixed bed, or as a fluidized bed.

In an embodiment, a suitable absorption solvent system may be capable of reversibly complexing with the ethylene and/or isobutane. Such an absorption solvent system may generally comprise a complexing agent and a solvent. In an embodiment, an absorption solvent system may be characterized as having a selectivity of ethylene to ethane where ethylene and ethane are present at the same partial pressure of about 40:1 at approximately 14 psi, about 12:1 at approximately 20 psi, about 6:1 at approximately 40 psi, and about 3:1 at approximately 180 psi partial pressure. In an embodiment, the solvent system may be further characterized as having a high contaminant tolerance and as exhibiting high stability at increased and/or fluctuating temperatures and/or pressures, or combinations thereof.

In an embodiment, the complexing agent may comprise a metallic salt. In such an embodiment, the metallic salt may comprise a salt of one or more transition metals and a weakly-ionic halogen. Non-limiting examples of suitable transition metals include silver, gold, copper, platinum, palladium, or nickel. Non-limiting example of suitable weakly-ionic halogens include chlorine and bromine. In an embodiment, a suitable transition metal salt may be characterized as having a high specificity for olefins. Non-limiting examples of suitable transition metal-halogen salts include silver chloride (AgCl) and copper chloride (CuCl). In a particular embodiment, the salt employed in the absorption solvent system comprises CuCl. Not seeking to be bound by theory, such a metallic salt may interact with the double carbon bonds of olefins (e.g., ethylene).

In an embodiment, the complexing agent may comprise a copper (I) carboxylate. In such an embodiment, suitable copper (I) carboxylates may comprise salts of copper (I) and mono-, di-, and/or tri-carboxylic acids containing 1-20 carbon atoms. The carboxylic acid component of the salt may comprise an aliphatic constituent, a cyclic constituent, an aryl constituent, or combinations thereof. Other suitable examples of copper (I) carboxylates include Cu(I) formate, Cu(I) acetate, Cu(I) propionate, Cu(I) butyrate, Cu(I) pentanoate, Cu(I) hexanoate, Cu(I) octanoate, Cu(I) decanoate, Cu(I) 2-ethyl-hexoate, Cu(I) hexadecanoate, Cu(I) tetradecanoate, Cu(I) methyl formate, Cu(I) ethyl acetate, Cu(I) n-propyl acetate, Cu(I) n-butyl acetate, Cu(I) ethyl propanoate, Cu(I) octoate, Cu(I) benzoate, Cu(I) p-t-butyl benzoate, and the like. In an additional embodiment, the complexing agent may comprise an adduct of a copper (I) carboxylate, for example, as disclosed herein, and boron trifluoride ($BF_3$).

In an additional and/or alternative embodiment, the complexing agent may comprise a copper (I) sulfonate. Non-limiting examples of suitable copper (I) sulfonates include the copper (I) salts of sulfonic acids having 4 to 22 carbon atoms. The sulfonic acid component of the salt may comprise an aliphatic constituent, a cyclic constituent, an aryl constituent, or combinations thereof. The aliphatic sulfonic acids can be straight chain or branched. Examples of suitable aliphatic sulfonic acids include, but are not limited to, n-butanesulfonic acid, 2-ethyl-1-hexanesulfonic acid, 2-methylnonanesulfonic acid, dodecanesulfonic acid, 2-ethyl-5-n-pentyltridecanesulfonic acid, n-eicosanesulfonic acid, and the like. Examples of suitable aromatic sulfonic acids include benzenesulfonic acid, alkylbenzenesulfonic acids wherein the alkyl member contains from 1 to 16 carbon atoms, such as p-toluenesulfonic acid, dodecylbenzenesulfonic acid (o-, m-, and p-), p-hexadecylbenzenesulfonic acid, and the like, naphthalenesulfonic acid, phenolsulfonic acid, naphtholsulfonic acids, and halobenzenesulfonic acids, such as p-chlorobenzenesulfonic acid, p-bromobenzenesulfonic acid, and the like.

In an embodiment where the complexing agent may further comprise a hindered olefin. For example, the complexing agent may comprise such a hindered olefin in an embodiment wherein the complexing agent forms a copper complex with insufficient solubility. An example of such a hindered olefin is a propylene tetramer (i.e. dodecene). Not intending to be bound by theory, the hindered olefin may increase the solubility of the copper complex while being easily displaced by ethylene.

In various embodiments, the complexing agent may comprise one or more of the complexing agents disclosed in U.S. Pat. Nos. 5,104,570; 5,191,153; 5,259,986; and 5,523,512, each of which is incorporated by reference in its entirety.

In an embodiment, the solvent may comprise an amine or an amine complex, an aromatic hydrocarbon, an olefin, or combinations thereof. Non-limiting examples of solvent amines include pyridine, benzylamine, and aniline. For examples, the amine may comprise an aniline (phenylamine, aminobenzene); alternatively, aniline combined with dimethylformamide (DMF), and in embodiments, aniline and N-methylpyrrolidone (NMP). In an embodiment where the solvent comprises an aromatic hydrocarbon, the aromatic hydrocarbon may comprise an unsubstituted or alkyl substituted aryl groups. In such an embodiment, the aromatic hydrocarbon may be in the liquid phase under normal, ambient conditions. Suitable non-limiting examples include toluene, xylene, and the like. In embodiments where the solvent comprises an olefin, non-limiting examples include olefins having 10 to 16 carbon atoms. For example, the olefin may comprise propylene tetramer, dodecene, tetradecene, hexadecene, or combinations thereof.

In an embodiment, the solvent may be characterized as aprotic, that is, as not including a dissociable hydrogen atom. Not intending to be bound by theory, a dissociable hydrogen solvent may result in the hydrogenation of the double bond between carbons in an olefin such as ethylene. Further, the solvent may be characterized as polar, as having a slight polarity, or as having unidirectional, electric charge. Not intending to be bound by theory, a polar solvent may interact with and at least partially solubilize the salt.

In an embodiment, the solvent may be characterized as a liquid produced industrially in relatively high volumes, having a relatively low cost, being easily transportable, or combinations thereof. The solvent may be further characterized as capable of retaining a complexed olefin-metal salt or retaining a weakly ionic metal salt despite fluctuations in temperature and/or pressure.

In an embodiment, the absorption solvent system may comprise copper chloride, aniline, and dimethylformamide (CuCl/aniline/DMF). In an alternative embodiment, the absorption solvent system may comprise copper chloride, aniline, and N-methylpyrrolidone (CuCl/aniline/NMP). In such an embodiment, a CuCl/aniline/NMP solvent system may be characterized as having increased volatile stability at lower pressures and higher temperatures. In alternative embodiments, the absorption solvent system may comprise copper (I) carboxylate and an aromatic solvent such as toluene or xylene. In alternative embodiments, the absorption solvent system may comprise copper (I) sulfonate and an aromatic solvent such as toluene or xylene. In alternative embodiments, the absorption solvent system may comprise an adduct of copper (I) carboxylate and $BF_3$ in an aromatic solvent such as toluene or xylene.

In an embodiment, the absorption solvent system may comprise copper (I) 2-ethyl-hexanoate and propylene tetramer. In an embodiment, the absorption solvent system may comprise copper (I) 2-ethyl-hexanoate and dodecene. In an embodiment, the absorption solvent system may comprise copper (I) hexadecanoate and hexadecene. In an embodiment, the absorption solvent system may comprise copper (I) tetradecanoate and tetradecene.

In an embodiment, allowing the at least one component to be absorbed by the absorbent may comprise allowing the at least one component to become reversibly bound, linked, bonded or combinations thereof to the absorbent or a portion thereof, for example, via the formation of various links, bonds, attractions, complexes, or combinations thereof. For example, in an embodiment where the absorbent comprises an absorption solvent system (e.g., a CuCl/aniline/DMF solvent system or a CuCl/aniline/NMP solvent system), allowing absorption of the at least one component may comprise allowing a complex to form between the absorbent and the at least one component, referred to as an absorbed component complex (e.g., an absorbed ethylene complex).

Allowing absorption of the at least one component may further comprise providing and/or maintaining a suitable pressure of the environment in which the gas stream and absorbent are brought into contact, providing and/or maintaining a suitable partial pressure of a gas, providing and/or maintaining a suitable temperature in the environment in which the gas stream and absorbent are brought into contact, catalyzing the absorption, or combinations thereof. Not intending to be bound by theory, the absorption of the at least one component by the absorbent may be improved at a suitable temperature and/or pressure.

In an embodiment, the absorption reactor 116 may be capable of selectively inducing thermal and/or pressure fluctuations, variations, or cycles. In an embodiment, the absorption reactor 116 may be configured to selectively absorb and/or induce the absorption of an unreacted ethylene monomer (and optionally, comonomer) from a composition comprising various other gases (e.g., ethane). In another embodiment, the absorption reactor 116 may be configured to selectively absorb and/or induce the absorption of butane, particularly, isobutane, from a composition comprising various other gases. In still another embodiment, the absorption reactor 116 may be configured to selectively absorb both unreacted ethylene and butane, particularly, isobutane, from a composition comprising various other gases (e.g., ethane).

Figure 7:
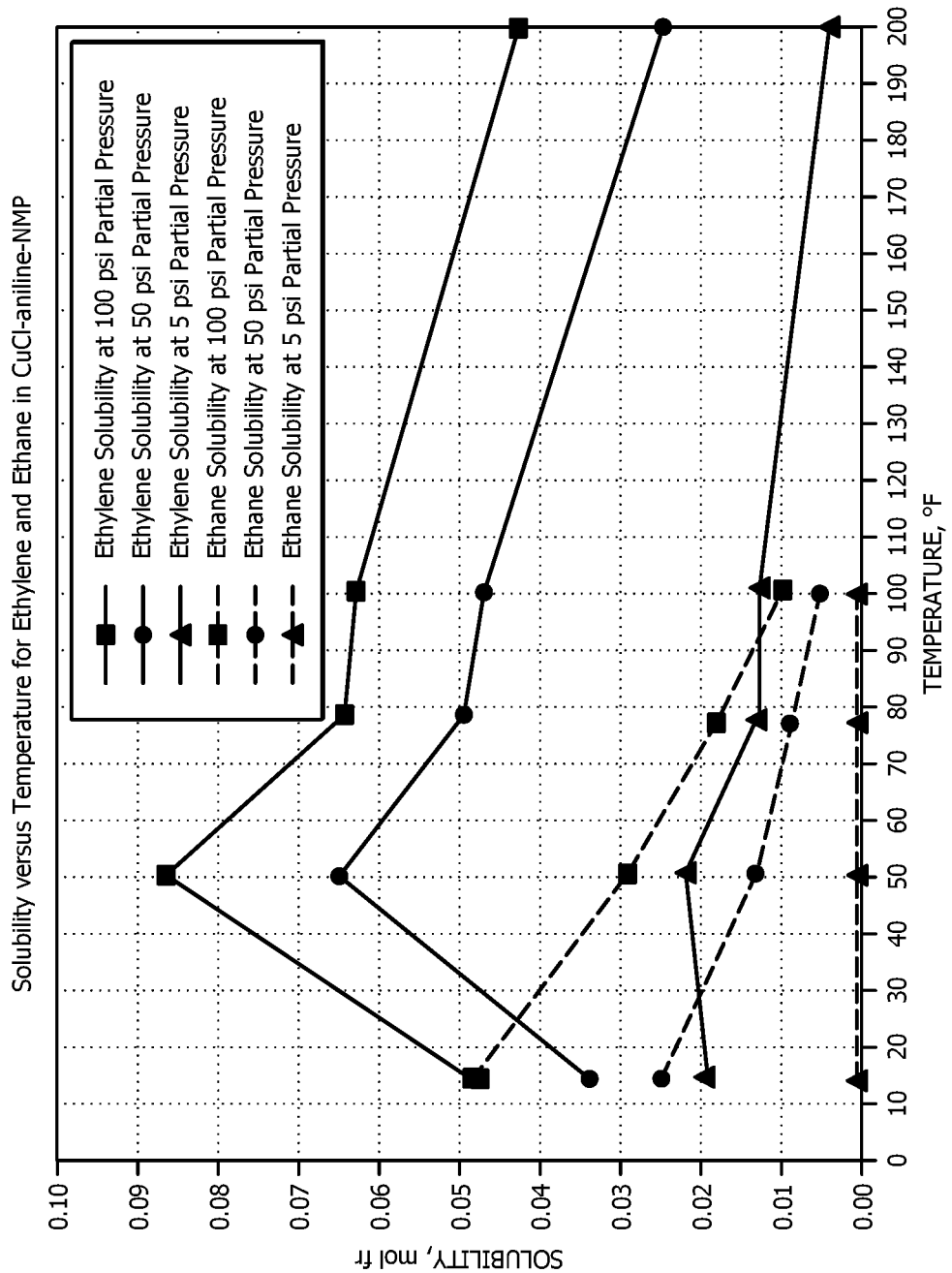
FIG. 7 is a graph illustrating solubility versus temperature for ethylene and ethane in an absorption solvent system.

In an embodiment, the absorption reactor 116 may be configured to provide or maintain a suitable temperature, for example, as may be dependent upon the phase in which the absorption reactor operates at a given time. For example, the absorption reactor 116 may be configured to provide or maintain a suitable temperature, for example, for the purpose of increasing absorption of a desired chemical species, decreasing absorption of a desired chemical species, flashing an unabsorbed gas from the reactor 116, recovering unreacted ethylene from the absorption reactor 116, regenerating absorbent in the absorption reactor 116, or combinations thereof. In an embodiment, such a suitable temperature may be in a range of from about 40° F. to about 110° F., alternatively, from about 40° F. to about 60° F., alternatively, from about 45° F. to about 55° F., alternatively, from about 50° F. to about 55° F., alternatively about 50° F. For example, it has been found the operating temperature of the absorption reactor 116 (and absorption solvent system) in a temperature range of from about 40° F. to about 110° F., alternatively, from about 40° F. to about 60° F., alternatively about 50° F. may yield an unexpected increase in the absorption of ethylene relative to the absorption of ethane. Not intending to be bound by theory, one skilled in the art will appreciate (for example, based on partial pressure concepts from Raoult's law) the expectation for solubility of ethylene and ethane in an absorbent solvent to increase at decreasing temperatures. However, contrary to such expectations, it has been found that the amount of ethylene absorbed in the absorbent solvent and/or the absorbent solvent system of the disclosed embodiments decreases as the temperature decreases below 50° F. Because of this unexpected phenomenon, absorption of ethylene may be greatest for temperatures in a range of from about 40° F. to about 110° F., alternatively, in a range of from about 40° F. to about 60° F., alternatively, at a temperature of about 50° F. FIG. 7 is graph showing the solubility at varying temperatures for ethylene and ethane in a copper chloride, aniline, NMP absorbent solvent system. The graph illustrates the expected solubility trend of ethane and the unexpected solubility trend of ethylene across the temperatures discussed above.

In an embodiment, the absorption reactor 116 may be configured to provide or maintain a suitable temperature in a range from about 40° F. to about 110° F. during absorption of one or more components of the gas stream (e.g., ethylene and/or isobutane). As disclosed above, it has been found that ethylene solubility is unexpectedly greatest at temperature in a range of from about 40° F. to about 60° F. In an embodiment, the absorption reactor 116 may be operated at a temperature of from about 40° F. to about 60° F., alternatively a temperature of about 50° F. during absorption of ethylene and/or isobutene from a gas stream. In an alternative embodiment, the absorption reactor may be operated at a temperature of from about 60° F. to about 110° F., or from about 70° F. to about 90° F. during absorption of ethylene and/or isobutene from a gas stream. For example, such absorption temperatures of the absorption reactor 116 may be suitable as an economic alternative to operating at a lower temperature (which may require energy expenditure with cooling, for example). For example, operating an absorption reactor, like absorption reactor 116, at temperatures in a range of from about 60° F. to about 110° F., or from about 70° F. to about 90° F. may require less energy, which may create a cost savings, by allowing the absorption reactor to be operated at the ambient temperature of a given geographic location.

In an embodiment, the absorption reactor 116 may be configured to provide or maintain a suitable pressure during operation. Such a suitable pressure may be in a range of from about 5 psig to about 500 psig, alternatively, from about 50 psig to about 450 psig, alternatively, from about 75 psig to about 400 psig. In an additional embodiment, the absorption reactor 116 may be configured to provide or maintain a suitable partial pressure of ethylene during operation. Such a suitable ethylene partial pressure may be in a range of from about 1 psia to about 400 psia, alternatively, from about 30 psia to about 200 psia, alternatively, from about 40 psia to about 250 psia, alternatively, from about 40 psia to about 75 psia, alternatively, from about 40 psig to about 60 psig, alternatively about 40 psig, alternatively, about 60 psig. Not intending to be bound by theory, pressurizing the absorption reactor 116 may facilitate absorption of ethylene and/or the formation of a complex of ethylene and the absorption solvent system (e.g., the CuCl/aniline/NMP system). Also, not intending to be bound by theory, the selectivity of the absorption solvent system for ethylene may increase with a decrease in the pressure of the absorption reactor.

In an embodiment, the absorption reactor 116 may be configured for batch and/or continuous processes. For example, in an embodiment, a PEP system may comprise two or more absorption reactors (e.g., such as absorption reactor 116), each of which may be configured for batch operation. For example, by employing two or more absorption reactors, such a system may be configured to allow for continuous operation by absorbing a component of a gas stream into a "first batch" in the first absorption reactor while a "second batch" is prepared for absorption in the second absorption reactor. As such, by cycling between two or more suitable reactors, a system may operate continuously.

Figure 8:
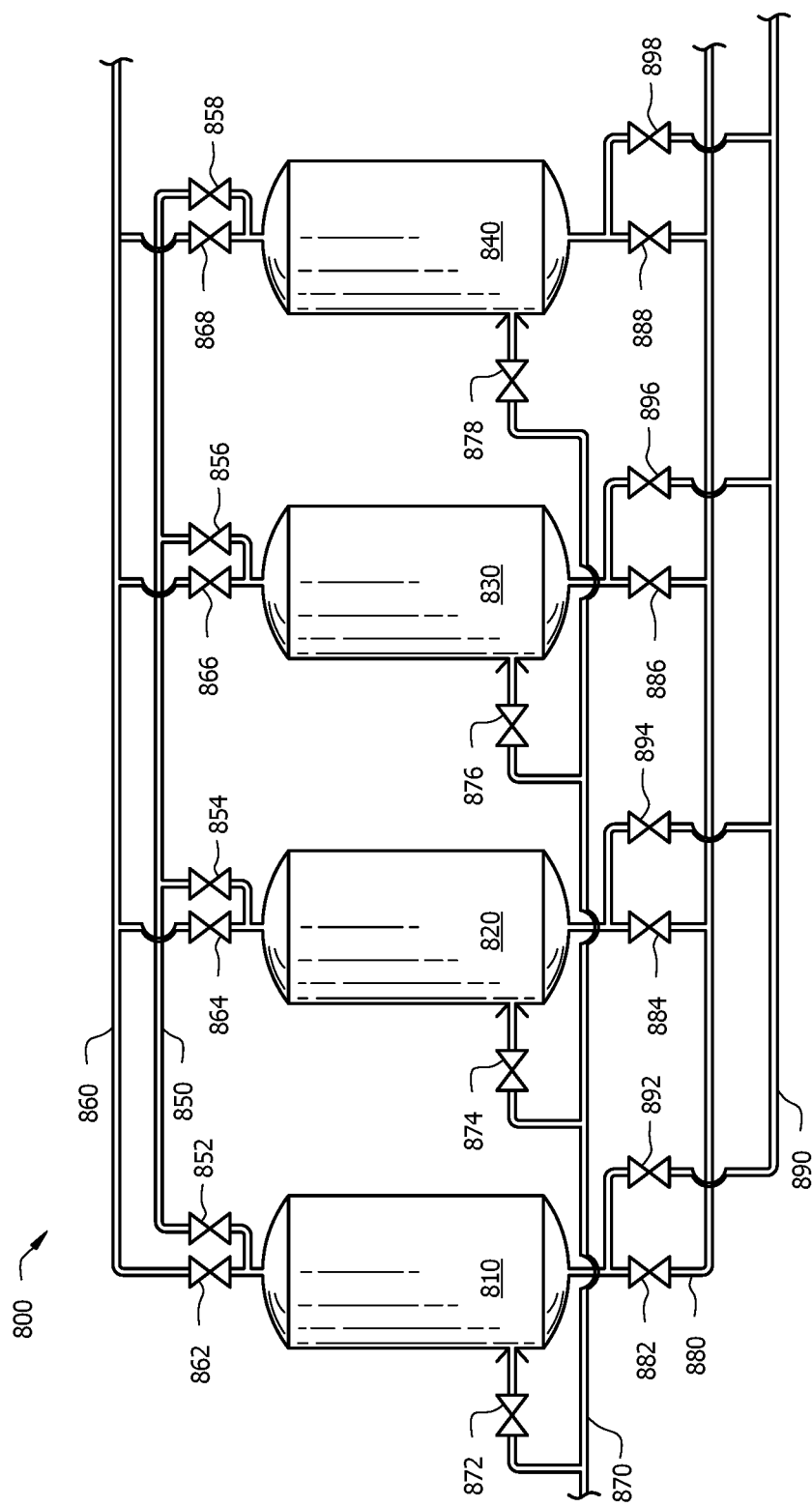
FIG. 8 illustrates a schematic of an embodiment of an absorption reactor having a pressure swing absorption configuration.

For example, in an embodiment two or more absorption reactors (e.g., an absorption reactor system) may be configured for pressure swing absorption (PSA) of ethylene using a liquid solvent, for example, the absorption solvent system or absorption solvent as disclosed herein. In such an embodiment, the absorption reactor 116 may include two or more absorption reactors configured for PSA (e.g., an absorption reactor system). FIG. 8, shows an absorption reactor system 800 with four absorption reactors 810, 820, 830, and 840 configured for PSA. Although the embodiment of FIG. 8 illustrates four absorption reactors (e.g., absorption reactors 810, 820, 830, and 840), one of skill in the art, upon viewing this disclosure, will recognize that two, three, five, six, seven, eight, or more absorption reactors may be similarly employed. In such an embodiment, the each of the absorption reactors may be configured substantially as disclosed herein. In an embodiment, one or more of the reactors 810, 820, 830, and 840 may be connected via a circulation system (for example, comprising one or more pumps, valves, conduits, and the like) to circulate the liquid solvent in the reactors 810, 820, 830, and 840 during absorption. The absorption reactors 810, 820, 830, and 840 may cycle between an absorption phase (in which a gaseous component, such as ethylene and/or isobutane, is absorbed by the absorption solvent and/or absorption solvent system) and a regeneration phase (in which the absorbed and/or complexed gaseous component is liberated from the absorption solvent system and/or the absorption solvent system is prepared for reuse, as will be disclosed herein). For example, the reactors 810, 820, 830, and 840 may be cycled between the absorption and regeneration phases (e.g., via one or more intermediate phases) on a coordinated basis so that not all reactors 810, 820, 830, 840 are undergoing absorption or regeneration at the same time. In an embodiment where absorption reactors 810, 820, 830, and 840 are configured to operate in PSA, the reactors 810, 820, 830, and 840 serve as both absorbers and as regenerators. In such an embodiment, separate vessels for regeneration may not be required (e.g., as disclosed herein).

As an example of PSA operation on a coordinated basis, at a given phase during such operation, reactor 810 may operate in the absorption phase, for example, at absorption conditions as disclosed herein. At substantially the same time, reactor 820 may be pressurized to an intermediate pressure, for example, below that of the absorption pressure. Also, at substantially the same time, reactor 830 may depressurize from an intermediate pressure to a regeneration pressure, and while reactor 840 may depressurize from an absorption pressure (from previously being in an absorption phase) to an intermediate pressure. Not intending to be bound by theory, depressurization (e.g., from the absorption pressure to the intermediate pressure and from the intermediate pressure to the regeneration pressure) of each of reactors 810, 820, 830, and/or 840 following absorption may allow the absorbed gaseous components (e.g., ethylene and/or isobutane) to be liberated from the absorbent and/or the absorbent to be regenerated (e.g., prepared for re-use, as disclosed herein). In an embodiment, the pressure from one or more of the reactors (e.g., reactors 810, 820, 830, and/or 840) may be utilized to pressurize another of these reactors. For example, in the embodiment of FIG. 8, the pressure of gas in reactor 840 may be used to pressurize reactor 820 to the intermediate pressure through line 850, with valves 858 and 884 being in an open position and valves 882 and 856 being in a closed position. Valves 862, 864, 866, and 868 may be switched between an open position and a closed position to allow product nitrogen in stream 860 to flow in and out of reactors 810, 820, 830, and 840. Valves 852, 854, 856, 858 may be switched between an open position and a closed position to allow pressurization and depressurization of reactors 810, 820, 830, and 840 through stream 850. Valves 882, 884, 886, 888 may be switched between an open position and a closed position to allow light gas stream 880 to feed to reactors 810, 820, 830, and 840 when in the absorption phase. Valves 892, 894, 896, and 898 may be switched between an open position and a closed position to remove any purge gas from reactors 810, 820, 830, and 840 through stream 890.

In an embodiment, a stripping gas, such as isobutane or nitrogen, may be added to the absorption reactors 810, 820, 830, and 840, for example, through stream 870 during the regeneration phase. Stream 870 may be positioned at a bottom of reactors 810, 820, 830, and 840 so the stripping gas may bubble through the reactor 810, 820, 830, or 840 (and through any packing materials therein). Valves 872, 874, 876, and 878 may be switched between open and closed positions to add the stripping gas to the reactors 810, 820, 830, and 840 during regeneration. Not intending to be bound by theory, the stripping gas may lower the partial pressure of ethylene in the absorption reactors 810, 820, 830, and 840 during regeneration.

In an embodiment, one or more of the absorption reactors 810, 820, 830, and 840 may comprise internals to distribute the gas through the liquid absorption solvent and prevent channeling. Suitable internals may include distillation packing that distributes gas and reduces axial mixing of the liquid. Internals may prevent liquid absorption solvent in the absorption reactors 810, 820, 830, and 840 from mixing so that solvent flow would be first saturated and then a saturation front may move vertically upward through the absorption reactors 810, 820, 830, and 840.

In an embodiment, separating at least one gaseous component from the gas stream comprises removing a waste stream. In an embodiment, the remaining unabsorbed gas stream components form the waste stream. In an embodiment where the absorbed component comprises ethylene and the absorbent comprises a CuCl/aniline/DMF or a CuCl/aniline/NMP solvent system, such a waste stream may comprise methane, ethane, acetylene, propylene, various other hydrocarbons, volatile contaminants, or combinations thereof. Further, such a waste stream may be substantially free of unreacted ethylene monomers or, optionally, comonomers. As used herein, "substantially free of unreacted ethylene monomers" means that the waste gases comprise less than 50% unreacted ethylene monomers, alternatively, less than 10% unreacted ethylene monomers, alternatively, less than 1.0% unreacted ethylene monomers, alternatively, less than 0.1 unreacted ethylene monomers, alternatively, less than 0.01% unreacted ethylene monomers by total weight of the stream.

In an embodiment, removing the waste stream may comprise cooling the waste stream, and/or reducing or increasing the waste stream pressure such that the waste stream flows to the processing device 114. For example, in an embodiment, the waste stream may be "swept away" by conveying a suitable sweep gas (e.g., an inert or unreactive gas, as disclosed above) through the vessel containing the waste gas (e.g., the absorption reactor 116) at a sufficient pressure, at velocity, or combinations thereof to expel the waste gases therefrom. For example, in the embodiments illustrated by FIGS. 1-3, separating at least one gaseous component from the gas stream yields a waste gas stream 20 being substantially free of unreacted ethylene monomers (optionally, comonomers), alternatively, a waste gas stream having a reduced concentration of unreacted ethylene monomers (optionally, comonomers). For example, the waste gas stream may comprise less than about 30%, alternatively, less than about 25%, alternatively, less than about 20%, alternatively, less than about 15%, alternatively, less than about 10% unreacted ethylene monomers by total weight of the stream. In an additional embodiment, the ethylene may be decreased by a percentage of the ethylene present in the gas stream prior to separating at least one gaseous component therefrom. For example, the waste gas stream may comprise less than about 40%, alternatively, less than about 30%, alternatively, less than about 20% by total weight of the stream of the unreacted ethylene monomers present in the gas stream prior to separation.

In an embodiment, separating at least one gaseous component from the gas stream may further comprise liberating the absorbed gaseous component from the absorbent (e.g., in situ within absorption reactor 116 and/or in another vessel such as regenerator 120). Liberating the absorbed gaseous component from the absorbent generally comprises any suitable means of reversing the various links, bonds, attractions, complexes, or combinations thereof by which the at least one gaseous component is bound, linked, bonded or combinations thereof to the absorbent or a portion thereof. Nonlimiting examples of a suitable means by which to liberate the absorbed gaseous component include altering absorption kinetics or the absorption equilibrium of the absorbent, heating or depressurizing the absorbent, altering the partial pressure of the absorbed gas, or combinations thereof.

In an embodiment, the absorbed gaseous component may be liberated (e.g., desorbed and/or decomplexed) from the absorbent within the one or more of such absorption reactors in a regeneration and/or desorption phase. For example, in the embodiment of FIGS. 1 and 2 (and/or, in an embodiment where the absorption reactor 116 is configured in a PSA configuration, as disclosed herein with respect to FIG. 8), the absorption reactor 116 may be configured to induce the release of the gas absorbed or complexed by the absorption solvent therefrom (e.g., desorption and/or decomplexation of the absorbed and/or complexed ethylene and/or isobutane), as disclosed in detail herein. Not intending to be bound by theory, inducing the release of the absorbed or complexed gas may comprise altering the reaction kinetics or the gas-solvent equilibrium of the absorption solvent system, the temperature of the absorption reactor 116, the pressure of the absorption reactor 116, the partial pressure of the absorbed gas, or combinations thereof. In such an embodiment, the absorption reactor 116 may comprise controls, thermal conduits, electric conduits, compressors, vacuums, the like, or combinations thereof configured to alter the reaction kinetics, the gas-solvent equilibrium, the temperature of the absorption reactor 116, the pressure of the absorption reactor 116, or combinations thereof.

For example, in an embodiment, liberating the absorbed gaseous component may comprise depressurizing the solution comprising the complexed ethylene to a suitable partial pressure. In an additional embodiment, liberating the absorbed gaseous component may comprise heating he solution comprising the complexed ethylene within the absorption reactor 116 (alternatively, within a regenerator 120, as disclosed herein below) to a suitable temperature. Such a suitable temperature may be in a range of from about 110° F. to about 200° F., alternatively, from about 140° F. to about 160° F., alternatively, from about 160° F. to about 200° F., alternatively, from about 180° F. to about 200° F., to encourage release of the absorbed compound (e.g., ethylene and/or isobutane) from the absorption solvent. For example, in a particular embodiment, the absorption reactor 116 (alternatively, the regenerator 120) may be operated at a temperature of from about 160° F. to about 200° F., alternatively, from about 180° F. to about 200° F. during the liberation of the absorbed component (e.g., ethylene and/or isobutene) from the absorption solvent. In an alternative embodiment, the absorption reactor 116 (alternatively, the regenerator 120) may be operated at a temperature of from about 140° F. to about 160° F. during the liberation of the absorbed component (e.g., ethylene and/or isobutene) from the absorption solvent. For example, such liberation temperatures may be suitable as an economic alternative. For example, operation an absorption reactor like absorption reactor 116 (alternatively, a regenerator like regenerator 120) at temperatures in a range of from about 140° F. to about 160° F. during the liberation of the absorbed component may require less energy, which may create a cost savings, by allowing heat derived from other sources (e.g., polymerization reactor coolant, low pressure stream, heat-exchangers upstream of regenerators, heat-exchangers in the absorbent recycle line, polymerization reactors, flash-line heaters, flash vessels, or the like, or combinations thereof) to be utilized to heat the absorption reactor and/or the regenerator.

Additionally, in such an embodiment, the absorption reactor 116 may be configured to evacuate gases (e.g., a previously absorbed and then released gas, such as ethylene) and/or to facilitate the release of the absorbed gas via a pressure differential. The absorption reactor 116 may be configured to provide or maintain a suitable partial pressure. Such a suitable partial pressure may be in a range of from about 0.1 psig to about 40 psig, alternatively, from about 5 psig to about 30 psig, alternatively, from about 5 psig to about 15 psig. In an embodiment, the absorption reactor 116 may be configured to provide or maintain an ethylene partial pressure in a range of from about 0 psia to about 5 psia.

In an alternative embodiment, separating at least one gaseous component from the gas stream may further comprise removing the solution comprising the absorbed component complex (e.g., the absorbed ethylene complex) for further processing. In such an alternative embodiment, the absorption complex comprising the absorbed gaseous component may be removed from the absorption reactor 116 to the regenerator 120 for liberation of the absorbed gaseous component and/or regeneration of the absorption complex as a complexed stream 28. In such an embodiment, the complexed stream 28 may comprise ethylene, ethane, and/or isobutane. Ethylene may be present in a range of from about 0.1% to about 10%, alternatively, from about 0.4% to about 5%, alternatively, from about 0.5% to about 2.5% by total weight of the stream. Ethane may be present in a range of from about 0.1% to about 1%, alternatively, from about 0.2% to about 0.5% by total weight of the stream. Isobutane may be present in a range of from about 0.1% to about 1%, alternatively, from about 0.2% to about 0.5% by total weight of the stream.

In one or more of the embodiments disclosed herein, separating a complexed stream into a recycle stream and an absorbent stream (e.g., at block 58) comprises liberating the absorbed gaseous component from the absorbent. As explained above, liberating the absorbed gaseous component from the absorbent generally comprises any suitable means for reversing the various links, bonds, attractions, complexes, or combinations thereof by which the at least one gaseous component is bound, linked, bonded or combinations thereof to the absorbent or a portion thereof. Various processes and/or parameters for liberating an absorbed gaseous component were disclosed above with respect to liberation within the absorption reactor.

In the embodiment illustrated by FIG. 3, separating a complexed stream into a recycle stream and an absorbent stream may comprise routing the complexed stream 28 to the regenerator 120. In one or more one or more of the embodiments disclosed herein, a regenerator 120 may comprise a device or apparatus configured to recover, regenerate, recycle, and/or purify an absorption solvent and/or to liberate an absorbed gas. Non-limiting examples of a suitable regenerator include a flash reactor, a depressurization reactor, a solvent regeneration reactor, or combinations thereof.

In an embodiment, regenerator 120 may be configured to operate on the basis of a pressure differential. In such an embodiment, the regenerator 120 may be configured to provide or maintain a suitable internal pressure. Such a suitable internal pressure may be in a range of from about 0 psig to about 150 psig, alternatively, from about 5 psig to about 30 psig, alternatively, from about 5 psig to about 15 psig, alternatively, from about 0 psig to about 10 psig. In an embodiment, the regenerator 120 may be configured to provide or maintain a suitable partial pressure. Such a suitable partial pressure may be in a range of from about 0 psia to about 50 psia.

In an embodiment, regenerator 120 may be configured to operate on the basis of an elevated temperature. Such a regenerator 120 may be configured to provide or maintain a suitable temperature. Such a suitable temperature may be in a range of from about 110° F. to about 200° F., alternatively, from about 140° F. to about 200° F., alternatively, from about 140° F. to about 160° F., alternatively, from about 160° F. to about 200° F., alternatively, from about 180° F. to about 200° F., to vaporize and/or release an absorbed compound (e.g., ethylene and/or isobutane) from the absorption solvent. In an embodiment, regenerator 120 (e.g., like the absorption reactor 116) may be heated to desorb, or regenerate, the absorption solvent system using heat sources comprising cooling water, low-pressure steam, or combinations thereof. Cooling water, low pressure steam, or a combination thereof may be suitable for heating regenerator 120 (or the absorption reactor 116, as disclosed above) to a temperature of from about 140° F. to about 200° F.

In an embodiment, the regenerator 120 may be configured for batch and/or continuous processes. For example, in an embodiment, a PEP system may comprise two or more absorption regenerators (e.g., such as regenerator 120), each of which may be configured for batch operation. As explained above, by employing two or more absorption reactors, such a system may operate to regenerate the absorbent continuously.

In an embodiment, separating a complexed stream into a recycle stream and an absorbent stream may yield a regenerated absorbent steam which may be reused in an absorption reaction and a recycle stream comprising unreacted monomers (optionally, comonomers) which may be reintroduced into or reused in a PEP process. For example, in the embodiment illustrated by FIG. 3, separating a complexed stream into a recycle stream and an absorbent stream 58 yields a recycle stream 22 which may be returned to the purifier 102 and a regenerated absorbent stream 30 which may be returned to the absorption reactor 116.

In an embodiment, liberating the absorbed gas may also yield a recycle stream comprising unreacted monomers (optionally, comonomers) which may be returned to the separator 108 for pressurization (e.g., via one or more compressors located at the separator 108). For example, in the embodiments illustrated by FIGS. 1-3, liberating the absorbed gas yields a recycle stream 22 which may be returned to the separator 108. Pressurizing the recycle stream 22 may yield a reintroduction stream 24 which may be reintroduced into or reused in a PEP process. For example, in the embodiments illustrated by FIGS. 1-3, a reintroduction stream 24 is introduced into the purifier 102. In an alternative embodiment, a recycle stream (such as recycle stream 22) may be pressurized and/or reintroduced into a PEP process without being returned to the separator 108. In an embodiment, the recycle stream 22 may comprise substantially pure ethylene; alternatively, the recycle stream 22 may comprise ethylene and butane, particularly, isobutane. In an embodiment, the gas stream may comprise may comprise nitrogen, ethylene, ethane, and/or isobutane. Ethylene may be present in a range of from about 65% to about 99%, alternatively, from about 70% to about 90%, alternatively, about 75% to about 85% by total weight of the stream. Ethane may be present in a range of from about 1% to about 20%, alternatively, from about 5% to about 15%, alternatively, from about 7.5% to about 12.5% by total weight of the stream. Isobutane may be present in a range of from about 1% to about 20%, alternatively, from about 5% to about 15%, alternatively, from about 7.5% to about 12.5% by total weight of the stream.

In one or more one or more of the embodiments disclosed herein, combusting a waste gas stream (e.g., at block 56) may generally comprise burning or incinerating one or more gaseous components of the waste gas stream 20. In one or more of the embodiments disclosed herein, combusting the waste gas stream 20 may further or alternatively comprise cracking, catalytic cracking, pyrolysis, dehydrogenating, scrubbing, converting, treating, or combinations thereof, of the waste gas stream 20 or combustion products.

As disclosed herein, the waste gas stream 20 may comprise volatilized solvents, unreacted gases, secondary products, contaminants, hydrocarbons, or combinations thereof. In an embodiment, the waste gas stream 20 may comprise hydrogen, nitrogen, methane, ethylene, ethane, propylene, propane, butane, isobutane, heavier hydrocarbons, or combinations thereof. Ethylene may be present in a range of from about 1% to about 40%, alternatively, from about 2.5% to about 20% by total weight of the stream. Ethane may be present in a range of from about 5% to about 50%, alternatively, from about 30% to about 40% by total weight of the stream. Isobutane may be present in a range from about 1% to about 20%, alternatively, from about 1.5% to about 5%, alternatively, from about 2% to about 3% by total weight of the stream. Nitrogen may be present in a range from about 10% to about 80%, alternatively, from about 35% to about 50%, alternatively, from about 40% to about 45% by total weight of the stream.

In embodiments as illustrated by FIGS. 1-3, combusting waste gas stream may comprise routing the waste gas stream 20 to the processing device 114. In one or more of the embodiments disclosed herein, the processing device 114 may comprise a combustion device or apparatus, such as a flare. Nonlimiting examples of a suitable flare include a torch, incinerator, the like, or combinations thereof. A flare may suitably comprise one or more controllable nozzles, an ignition source, a bypass valve, a pressure relief valve, or combinations thereof. The flare may be configured to provide an environment for the combustion of various waste products, for example, atomic gases (e.g. nitrogen, oxygen), oxides (e.g. carbon monoxide, oxides of nitrogen or sulfur), various unwanted gaseous products, or combinations thereof. In an embodiment, the flare may additionally comprise a device or apparatus configured to selectively remove one or more of contaminants prior to, during, and/or after combustion (e.g., such that a given combustion product is not released into the atmosphere).

In one or more of the embodiments disclosed herein, the processing device 114 may comprise a cracker, catalytic cracker, scrubber, converter, treater, dehydrogenator, deoxygenator, or combinations thereof, for example. In an embodiment, processing device 114 may comprise an ethylene cracker. In the processing device 114, one or more gaseous components, such as ethane, from waste gas stream 20 may be converted to a desired product, such as ethylene monomer. The desired product formed in the processing device 114 may be recycled to one or more of purifier 102, reactor 104, reactor 106, for example.

In other alternative embodiments, waste gas stream 20 may be used as fuel (for example for steam generation or co-gen operations, and/or may be used as fuel and/or a feed to a thermal cracking unit to form ethylene (e.g., to form feed stream 10). In another alternative embodiment, the waste gas from waste gas stream 20 may be exported from the plant to a monomer plant.

In an embodiment, implementation of one or more of the disclosed systems (e.g., PEP systems 100, 200, and/or 300) and/or processes (e.g., PEP processes 400, 500, and/or 600) may allow for the recovery of a substantial portion of the ethylene monomers that would otherwise be lost due to the operation of such systems or processes, for example, by flaring. In an embodiment, one or more of the disclosed systems may allow for the recovery of up to about 75%, alternatively, up to about 85%, alternatively, up to about 90%, alternatively, up to about 95% by total weight of the stream of the ethylene monomers that would otherwise be lost. In an embodiment, one or more of the disclosed systems may allow for the recovery of up to about 75%, alternatively, up to about 85%, alternatively, up to about 90%, alternatively, up to about 95% by total weight of the stream of the isobutane that would otherwise be lost. The recovery of such a portion of the unreacted ethylene monomers may yield a significant economic benefit, for example, by improving the efficiency of usage of ethylene monomers and decreasing capital inputs associated with the acquisition of ethylene monomers. Similarly, the recovery of such a portion of isobutane may yield a significant economic benefit, for example, by decreasing capital inputs associated with the acquisition of isobutane and/or by reducing the presence of isobutane in flare emissions.

In an embodiment, implementation of one or more of the disclosed systems and/or processes may decrease the amount of ethane that is returned to a polymerization reactor (such as reactors 104 and/or 106) via a recycle stream. By decreasing the amount of ethane contained in a stream recycled to a polymerization reactor, the overall efficiency of the polyethylene production may be improved (for example, by increasing the ethylene concentration without reaching the bubble point in the loop reactor). For example, decreasing the amount of ethane in a recycled stream may improve polymerization reactor efficiency, improve catalyst efficiency, reduce polymer fouling, reduce polymerization downtime, or combinations thereof.

A skilled artisan will recognize that industrial and commercial polyethylene manufacturing processes may necessitate one or more, often several, compressors or similar apparatuses. Such compressors are used throughout polyethylene manufacturing, for example to pressurize reactors 104, 106 during polymerization. Further, a skilled artisan will recognize that a polyethylene manufacturing process includes one or more deoxygenators and/or similar de-oxidizing apparatuses, for instance purifying solvents or reactants and/or for purging reactors of oxygen. Because the infrastructure and the support therefore, for example to provide power and maintain the compressors and/or deoxygenators, already exists within a commercial polyethylene manufacturing plant, reallocating a portion of these available resources for use in the disclosed systems may necessitate little, if any, additional capital expenditure in order to incorporate the disclosed systems and or processes.

Further, because compressors, deoxygenators, and various other components are already employed in various polyethylene processes and systems, the opportunity for increased operation of such apparatuses may improve the overall efficiency of polyethylene production systems and processes. For example, when a portion of a PEP process or system is taken off-line for maintenance and/or repair, other portions of the system (e.g., a compressor, a deoxygenator, a reactor, etc.) may continue to provide service according to the current processes. Operating and/or reallocating resources for operation of the disclosed PEP systems and/or processes may thereby increase the efficiency with which conventional systems are used.

Additional Description

A process and system for the production for polyethylene has been described. The following clauses are offered as further description:

Embodiment A

A process for recovery of ethylene from a polymerization product stream of a polyethylene production system, comprising:
separating a light gas stream from the polymerization product stream, wherein the light gas stream comprises ethane and unreacted ethylene;
contacting the light gas stream with an absorption solvent system, wherein the contacting the light gas stream with the absorption solvent system occurs at a temperature in a range of from about 40° F. to about 110° F., wherein at least a portion of the unreacted ethylene from the light gas stream is absorbed by the absorption solvent system; and
recovering unreacted ethylene from the absorption solvent system to yield recovered ethylene.

Embodiment B

The process of embodiment A, wherein the absorption solvent system comprises copper chloride, aniline, and N-methylpyrrolidone.

Embodiment C

The process of embodiments A through B, wherein the contacting the light gas stream with the absorption solvent system occurs at a temperature in a range of from about 40° F. to about 60° F.

Embodiment D

The process of embodiments A through C, wherein the contacting the light gas stream with the absorption solvent system occurs at a temperature of about 50° F.

Embodiment E

The process of embodiments A through B, wherein the contacting the light gas stream with the absorption solvent system occurs at a temperature in a range of from about 60° F. to about 90° F.

Embodiment F

The process of embodiments A through E, further comprising:
introducing a stripping gas into the absorption solvent system, wherein at least a portion of the stripping gas is absorbed by the absorption solvent system.

Embodiment G

The process of embodiment F, wherein the stripping gas is selected from the group consisting of nitrogen and isobutane.

Embodiment H

The process of embodiments A through G, wherein the contacting the light gas stream with the absorption solvent system comprises bubbling the light gas stream through a packed bed in the absorption solvent system.

Embodiment I

The process of embodiments A through H, wherein the contacting the light gas stream with the absorption solvent system comprises pressurizing the light gas stream and the absorption solvent system to a pressure in a range of from about 40 psig to about 60 psig.

Embodiment J

The process of embodiments A through I, wherein the recovering unreacted ethylene from the absorption solvent system comprises depressurizing the absorption solvent system having absorbed unreacted ethylene at a temperature in a range of from about 110° F. to about 200° F.

Embodiment K

The process of embodiments A through J, wherein the depressurizing the absorption solvent system occurs at a pressure in a range of from about 0 psig to about 10 psig.

Embodiment L

The process of embodiments A through K, wherein the depressurizing the absorption solvent system having absorbed unreacted ethylene occurs at a temperature in a range of from about 140° F. to about 160° F.

Embodiment M

The process of embodiments A through K, wherein the depressurizing the absorption solvent system having absorbed unreacted ethylene occurs at a temperature in a range of from about 160° F. to about 200° F.

Embodiment N

The process of embodiments A through M, further comprising:
removing at least a portion of elemental oxygen or oxygen-containing compounds from the light gas stream before contacting the light gas stream with the absorption solvent system.

Embodiment O

A polyethylene production process, comprising:
contacting ethylene and a polymerization catalyst in a polymerization reactor under suitable reaction conditions to yield a polymerization product stream;

separating a light gas stream from the polymerization product stream, wherein the light gas stream comprises unreacted ethylene;

contacting the light gas stream with an absorption solvent system in an absorption reactor at a temperature in a range of from about 40° F. to about 110° F., wherein at least a portion of the unreacted ethylene from the light gas stream is absorbed by the absorption solvent system to yield a composition comprising a complex of the absorption solvent system and unreacted ethylene;

removing unabsorbed gases of the light gas stream from contact with the absorption solvent system;

recovering unreacted ethylene from the absorption solvent system; and contacting the recovered ethylene and the polymerization catalyst.

Embodiment P

The process of embodiment 0, further comprising:

introducing a stream comprising the composition comprising the complex of the absorption solvent system and unreacted ethylene into a solvent regenerator at a temperature in a range of about 50° F. to about 200° F.;

recovering unreacted ethylene from the composition comprising the complex of the absorption solvent system and unreacted ethylene to yield recovered ethylene and a regenerated absorption solvent system;

introducing a stream comprising the recovered ethylene into the polymerization reactor; and introducing a stream comprising the regenerated absorption solvent system into the absorption reactor.

Embodiment Q

The process of embodiments O through P, wherein the introducing a stream comprising the composition comprising the complex of the absorption solvent system and unreacted ethylene into a solvent regenerator occurs at a pressure in a range of about 0 psig to about 10 psig.

Embodiment R

The process of embodiment 0, wherein the recovering unreacted ethylene from the absorption solvent system comprises depressurizing the absorption reactor to a pressure in a range of from about 0 psig to about 10 psig.

Embodiment S

The process of embodiments A through R, further comprising:

removing unabsorbed gases of the light gas stream from contact with the absorption solvent system to form a waste gas stream.

Embodiments T

The process of embodiment S, further comprising:

processing the waste gas stream in a processing device, wherein the processing device comprises a cracker, catalytic cracker, scrubber, converter, treater, dehydrogenator, deoxygenator, flare or combinations thereof.

Embodiment U

The process of embodiments O through T, wherein the absorption solvent system comprises copper chloride, aniline, and N-methylpyrrolidone.

Embodiment V

The process of embodiments O, R through U, wherein the contacting the light gas stream with the absorption solvent system in an absorption reactor comprises pressurizing the absorption reactor to a pressure in a range of from about 40 psig to about 60 psig.

Embodiment W

The process of embodiments O through V, further comprising:

removing at least a portion of elemental oxygen or oxygen-containing compounds from the light gas stream before introducing the light gas stream into the absorption reactor.

Embodiment X

A polyethylene production system, comprising:

a feed stream comprising ethylene, wherein the feed stream is characterized by introduction into a polymerization reactor;

a polymerization product stream, wherein the polymerization product stream is characterized by emission from the polymerization reactor and introduction into a separator;

a light gas stream comprising unreacted ethylene, wherein the light gas stream is characterized by emission from the separator, the light gas stream having been separated from the polymerization product stream, wherein the light gas stream is characterized by introduction into an absorption solvent system, wherein the absorption solvent system has a temperature in a range of from about 40° F. to about 110° F.;

an absorbent-ethylene conjugant, wherein the absorbent-ethylene conjugant is characterized by formation within the absorption solvent system by absorption of at least a portion of the unreacted ethylene by the absorption solvent system; and a waste gas stream comprising ethane, wherein the waste gas stream is characterized by emission from the absorption reactor, wherein the waste gas stream comprises components of the light gas stream that are not absorbed by the absorption solvent system; and a recovered unreacted ethylene stream, wherein the recovered unreacted ethylene stream is characterized by emission from the absorption reactor and reintroduction into the polymerization reactor.

Embodiment Y

The system of embodiment X, wherein recovery of the recovered unreacted ethylene from the absorbent-ethylene conjugant occurs via a pressure reduction from a pressure of the absorption reactor to a pressure in a range of from about 0 psig to about 10 psig.

Embodiment Z

The system of embodiments X through Y, wherein recovery of the recovered unreacted ethylene from the absorbent-ethylene conjugant occurs at a temperature in a range of about 110° F. to about 200° F.

Embodiment AA

The system of embodiments X through Z, wherein the absorption solvent system comprises copper chloride, aniline, and N-methylpyrrolidone.

Embodiment AB

A polyethylene production system, comprising:
a polymerization reactor, wherein the polymerization reactor is configured to receive a feed stream comprising ethylene, and wherein the polymerization reactor is configured to emit a polymerization product stream;
a separator, wherein the separator is configured to receive the polymerization product stream and to emit a light gas stream comprising unreacted ethylene, wherein the light gas stream has been separated from the polymerization product stream; and
an absorption reactor comprising an absorption solvent system, wherein the absorption reactor is configured to receive the light gas stream, to absorb at least a portion of the unreacted ethylene with the absorption solvent system at a temperature in a range of from about 40° F. to about 110° F., and to emit a waste gas stream comprising components of the light gas stream that are not absorbed by the absorption solvent system, and wherein the absorption reactor is further configured to emit a recovered unreacted ethylene stream, and wherein the polymerization reactor is further configured to receive the recovered unreacted ethylene stream.

Embodiment AC

The system of embodiment AB, wherein the recovered unreacted ethylene is recovered from the absorption solvent system via a pressure reduction from a pressure of the absorption reactor to a pressure in a range of from about 0 psig to about 10 psig.

Embodiment AD

The system of embodiments AB through AC, wherein the recovered unreacted ethylene is recovered from the absorption solvent system via a temperature increase from the absorption temperature to a temperature in a range of from about 110° F. to about 200° F.

Embodiment AE

The system of embodiments AB through AD, wherein the absorption reactor comprises two or more packed-bed reactors, wherein the recovered unreacted ethylene is recovered from the absorption solvent system via a pressure reduction of one of the two or more packed-bed reactors while another of the packed bed reactors operates at a pressure in a range of from about 40 psig to about 60 psig.

Embodiment AF

The system of embodiments AB through AE, wherein the absorption solvent system comprises copper chloride, aniline, and N-methylpyrrolidone.

Embodiment AG

The system of embodiments AB through AF, further comprising a second absorption reactor, wherein the absorption reactors are configured to absorb ethylene in a liquid solvent through pressure swing absorption.

Embodiment AH

A polyethylene production system, comprising:
a polymerization reactor, wherein the polymerization reactor is configured to receive a feed stream comprising ethylene, and wherein the polymerization reactor is configured to emit a polymerization product stream;
a separator, wherein the separator is configured to receive the polymerization product stream and to emit a light gas stream comprising unreacted ethylene, wherein the light gas stream has been separated from the polymerization product stream;
an absorption reactor comprising an absorption solvent system, wherein the absorption reactor is configured to receive the light gas stream, to absorb at least a portion of the unreacted ethylene with the absorption solvent system at a temperature in a range of from about 40° F. to about 110° F. and to emit a waste gas stream comprising components of the light gas stream that are not absorbed by the absorption solvent system, wherein the absorption reactor is further configured to emit a complexed stream comprising ethylene absorbed in the absorbent solvent system; and
a solvent regenerator to regenerate the absorption solvent system, and to emit a recovered unreacted ethylene stream, wherein the polymerization reactor is further configured to receive the recovered unreacted ethylene stream.

Embodiment AI

The system of embodiment AH, wherein the solvent regenerator is configured to operate at a pressure in a range of from about 0 psig to about 10 psig.

Embodiment AJ

The system of embodiments AH through AI, wherein the solvent regenerator is configured to operate at a temperature in a range of from about 110° F. to about 200° F.

Embodiment AK

The system of embodiments X through AJ, further comprising a processing device configured to receive the waste gas stream.

Embodiment AL

The system of embodiment AK, wherein the processing device comprises a cracker, catalytic cracker, scrubber, converter, treater, dehydrogenator, deoxygenator, flare or combinations thereof.

EXAMPLES

The disclosure having been generally described, the following examples are given as particular embodiments of the disclosure and to demonstrate the practice and advantages thereof. It is understood that these examples are given by way of illustration and is not intended to limit the specification or the claims in any manner.

Figure 9:
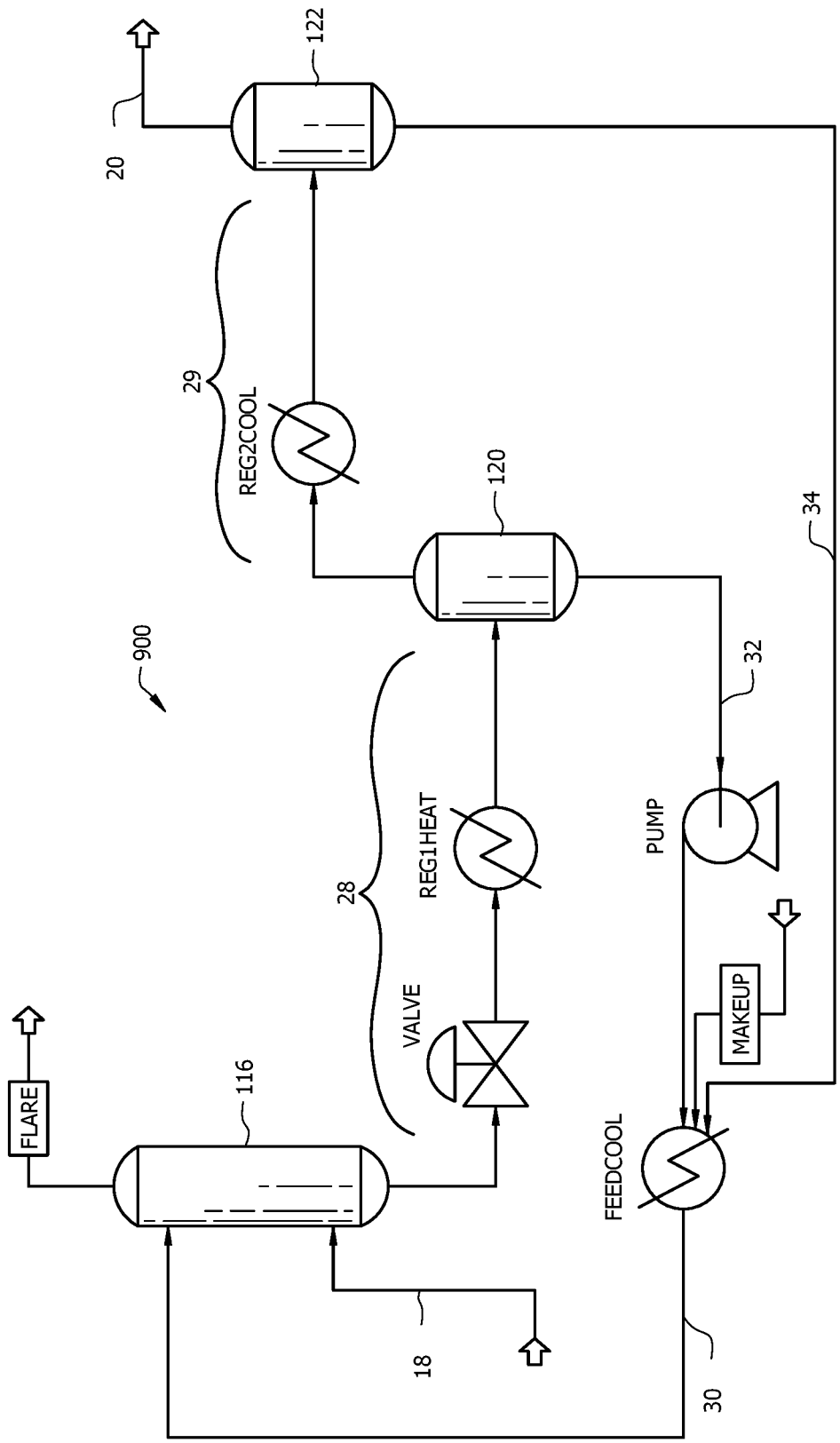
FIG. 9 illustrates a schematic of an embodiment of an absorption system.

A computerized commercial process simulator was employed to generate an output from a model in accordance with the systems and/or processes disclosed herein. The model employed is illustrated at FIG. 9, which shows an embodiment of a system 900, as disclosed herein, and shall be used to describe the examples below. In the embodiment shown in FIG. 9, a light gas stream 18, which was separated from a polymerization product stream of a polyethylene reactor, feeds to an absorption reactor 116. The total molar and mass flows and component molar and mass flows of the light gas stream 18 are shown in Table 1 below:

TABLE 1

| Total Molar Flow (lbmol/hr) | 52.9 | Total Mass Flow (lb/hr) | 1127 |
|---|---|---|---|
| Component Molar Flow (lbmol/hr) | | Component Mass Flow (lb/hr) | |
| Hydrogen | 15.4 | Hydrogen | 31 |
| Nitrogen | 4.9 | Nitrogen | 137 |
| Ethylene | 26 | Ethylene | 729 |
| Ethane | 5.6 | Ethane | 169 |
| Isobutane | 1.1 | Isobutane | 62 |
| Component Molar Fraction | | Component Mass Fraction | |
| Hydrogen | 0.291 | Hydrogen | 0.028 |
| Nitrogen | 0.092 | Nitrogen | 0.121 |
| Ethylene | 0.491 | Ethylene | 0.646 |
| Ethane | 0.106 | Ethane | 0.150 |
| Isobutane | 0.020 | Isobutane | 0.055 |

Unreacted ethylene that enters the absorption reactor 116 is absorbed in the absorption solvent system within the absorption reactor 116. Absorbed unreacted ethylene flows, as complexed stream 28, to a first regenerator 120. In stream 28, the absorbed ethylene is heated by heat exchanger REG1HEAT before entering the first regenerator 120. Ethylene desorbs from the solvent from the absorption solvent system in first regenerator 120 and flows through stream 29 to a second regenerator 122. Stream 29 may be cooled with heat exchanger REG2COOL before entering the second regenerator 122. Ethylene is recovered in stream 20. Absorption solvent in streams 32 and 34 combine in heat exchanger FEEDCOOL to recycle to the absorption reactor 116 in stream 30.

Table 2 shows operating conditions for examples 1-44 of ethylene recovery using the system 900 of FIG. 9. For the examples shown in Table 2, the absorption solvent system comprises a copper chloride, aniline, and NMP system, as disclosed herein, and composition of the purified product is based on 90% ethylene recovery. The composition of the purified product recovered in FIG. 9 comprises ethylene, ethane, nitrogen, hydrogen, and isobutane. The wt % of each of these components in the purified product is shown in Table 2. The purified product compositions shown in Table are compositions of stream 20 in FIG. 9. Select examples from Table 2 are discussed in detail below.

Example 3

In Example 3 of Table 2, the absorption reactor 116 in FIG. 9 operates at a temperature of 15° F., with a lean solvent temperature of 14° F. and pressure of 40 psig. The first regenerator 120 operates at a temperature of 150° F. and pressure of 0 psig. The second regenerator 122 operates at a temperature of 50° F. and pressure of 0 psig. Under these conditions, system 900 recovers 90% of the ethylene and the solvent circulation flow rate to 344,776 lb/hr and the amount of ethylene in the purified product to 64.5%.

Example 4

In Example 4 of Table 2, the operating conditions are the same as Example 3, except the first regenerator 120 operates at a temperature of 200° F. and pressure of 0 psig. Under these conditions, system 900 recovers 90% of ethylene for a solvent circulation flow rate of 143,736 lb/hr, and the purified product contains 77.5% ethylene.

Example 7

In Example 7 of Table 2, the absorption reactor 116 in FIG. 9 operates at a temperature of 53° F., with a lean solvent temperature of 50° F. Absorption reactor 116 also operates at a pressure of 40 psig. The first regenerator 120 operates at a temperature of 150° F. and a pressure of 0 psig. The second regenerator 122 operates at a temperature of 50° F. and a pressure of 0 psig. Under these conditions, system 900 recovers 90% of the ethylene for a solvent circulation flow rate of 53,920 lb/hr. The purified product composition for Example 7 is shown in Table 2.

When comparing Example 7 with the Examples 3 and 4, the solvent circulation flow rate of 53,920 lb/hr in Example 7 is less than the flow rates of 143,736 lb/hr and 344,776 lb/hr in the Examples 3 and 4. Thus, Example 7 shows the solvent circulation flow rate required to absorb ethylene in a copper chloride aniline NMP absorption solvent system is much less for an absorption temperature of 53° F. than for an absorption temperature of 15° F. because of the unexpected drop in solubility for ethylene in the absorption solvent system for temperatures below about 50° F.

Example 8

In Example 8 of Table 2, the absorption reactor 116 in FIG. 9 operates at a temperature of 55° F., with a lean solvent temperature of 50° F. Absorption reactor 116 also operates at a pressure of 40 psig. The first regenerator 120 operates at a temperature of 200° F. and a pressure of 0 psig. The second regenerator 122 operates at a temperature of 50° F. and a pressure of 0 psig. Under these conditions, system 800 recovers 90% of the ethylene for a solvent circulation flow rate of 47,785 lb/hr. The purified product composition for Example 8 is shown in Table 2.

Example 8 confirms the results shown in Example 7 that lower solvent circulation flow rates are required when the absorption reactor 116 operates at a temperature of 55° F. instead of temperatures below 50° F. Example 2 additionally shows varying the temperature of the regenerators 120 from 150° F. to 200° F. does not affect the solvent circulation flow rate to a significant degree.

Example 19

In Example 19 of Table 2, the absorption reactor 116 in FIG. 9 operates at a temperature of 53° F., with a lean solvent temperature of 50° F. Absorption reactor 116 also operates at a pressure of 40 psig. The first regenerator 120 operates at a temperature of 200° F. and a pressure of 10 psig. The second regenerator 122 operates at a temperature of 50° F. and a pressure of 10 psig. Under these conditions, system 900 recovers 90% of the ethylene for a solvent circulation flow rate of 59,272 lb/hr. The purified product composition is shown in Table 2.

Example 19 confirms the lower solvent circulation rates discussed in Examples 7 and 8 when compared to Examples 3 and 4. Example 19 also shows varying the pressure of the first and second regenerators 120 and 122 between 0 psig and 10 psig does not significantly alter results. Operation of the regenerators 120 and 122 at 0 psig may provide a lower solvent circulation rate as well as enhanced product purity, and operation of the regenerators 120 and 122 at 10 psig may provide a safer design because a positive pressure in the regenerators 120 and 122 reduces a chance of air and water infiltration via leaks in the system and process, which may react with copper chloride in the absorption solvent system and inhibit performance.

Example 28

In Example 28 of Table 2, the absorption reactor 116 in FIG. 9 operates at 52° F., with a lean solvent temperature of 50° F. Absorption reactor 116 also operates at a pressure of 60 psig. The first regenerator 120 operates at a temperature of 100° F. and a pressure of 0 psig. The second regenerator 122 operates at a temperature of 50° F. and a pressure of 0 psig. Under these conditions, system 900 recovers 90% of the ethylene for a solvent circulation flow rate of 58,613 lb/hr. The purified product composition is shown in Table 2.

Under the conditions in Example 28, the solvent circulation flow rate is less than that of the Examples 3 and 4, and the amount of ethylene in the purified product is significantly higher.

Example 29

In Example 29 of FIG. 2, the absorption reactor 116 in FIG. 9 operates at 55° F., with a lean solvent temperature of 50° F. Absorption reactor 116 also operates at a pressure of 60 psig. The first regenerator 120 operates at a temperature of 150° F. and a pressure of 0 psig. The second regenerator 122 operates at a temperature of 50° F. and a pressure of 0 psig. Under these conditions, system 900 recovers 90% of the ethylene for a circulation flow rate of solvent of 51,106 lb/hr. The purified product composition is shown in Table 2.

Under the conditions in Example 29, the solvent circulation flow rate is less than that of the Examples 3 and 4, and the amount of ethylene in the purified product is significantly higher.

Example 30

In Example 30 of Table 2, the absorption reactor 116 in FIG. 9 operates at 56° F., with a lean solvent temperature of 50° F. Absorption reactor 116 also operates at a pressure of 60 psig. The first regenerator 120 operates at a temperature of 200° F. and a pressure of 0 psig. The second regenerator 122 operates at a temperature of 50° F. and a pressure of 0 psig. Under these conditions, system 900 recovers 90% of the ethylene for a circulation flow rate of solvent of 46,744 lb/hr. The purified product composition is shown in Table 2.

Under the conditions in Example 30, the solvent circulation flow rate is less than that of the Examples 3 and 4, and the amount of ethylene in the purified product is significantly higher.

Example 33

In Example 33 of Table 2, the absorption reactor 116 in FIG. 9 operates at a temperature of 102° F., with a lean solvent temperature of 100° F. Absorption reactor 116 also operates at a pressure of 60 psig. The first regenerator 120 operates at a temperature of 200° F. and a pressure of 0 psig. The second regenerator 122 operates at a temperature of 50° F. and a pressure of 0 psig. Under these conditions, system 900 recovers 90% of the ethylene for a solvent circulation flow rate of 63,435 lb/hr. The purified product composition for Example 33 is shown in Table 2.

Under the conditions in Example 33, the solvent circulation flow rate is less than that of the Examples 3 and 4, and the amount of ethylene in the purified product is significantly higher. Moreover, Example 33 show that operation of the absorption reactor 116 at temperatures higher than the temperatures of maximum solubility shown in FIG. 7, for example, at 102° F. as shown in Example 33, may still prove economically feasible because, for example, solvent circulation flow rates remain low compared with conditions of Examples 3 and 4.

Example 40

In Example 40 of Table 2, the absorption reactor 116 in FIG. 9 operates at a temperature of 52° F., with a lean solvent temperature of 50° F. Absorption reactor 116 also operates at a pressure of 60 psig. The first regenerator 120 operates at a temperature of 150° F. and a pressure of 10 psig. The second regenerator 122 operates at a temperature of 50° F. and a pressure of 10 psig. Under these conditions, system 900 recovers 90% of the ethylene for a solvent circulation flow rate of 57,441 lb/hr. The purified product composition for Example 40 is shown in Table 2.

Under the conditions in Example 40, the solvent circulation flow rate is less than that of the Examples 3 and 4, and the amount of ethylene in the purified product is significantly higher.

Example 41

In Example 41 of Table 2, the absorption reactor 116 in FIG. 9 operates at 55° F., with a lean solvent temperature of 50° F. Absorption reactor 116 also operates at a pressure of 60 psig. The first regenerator 120 operates at a temperature of 200° F. and a pressure of 10 psig. The second regenerator 122 operates at a temperature of 50° F. and a pressure of 10 psig. Under these conditions, system 900 recovers 90% of the ethylene for a circulation flow rate of solvent of 51,482 lb/hr. The purified product composition is shown in Table 2.

Under the conditions in Example 41, the solvent circulation flow rate is less than that of the Examples 3 and 4, and the amount of ethylene in the purified product is significantly higher.

Example Simulation

Figure 10:
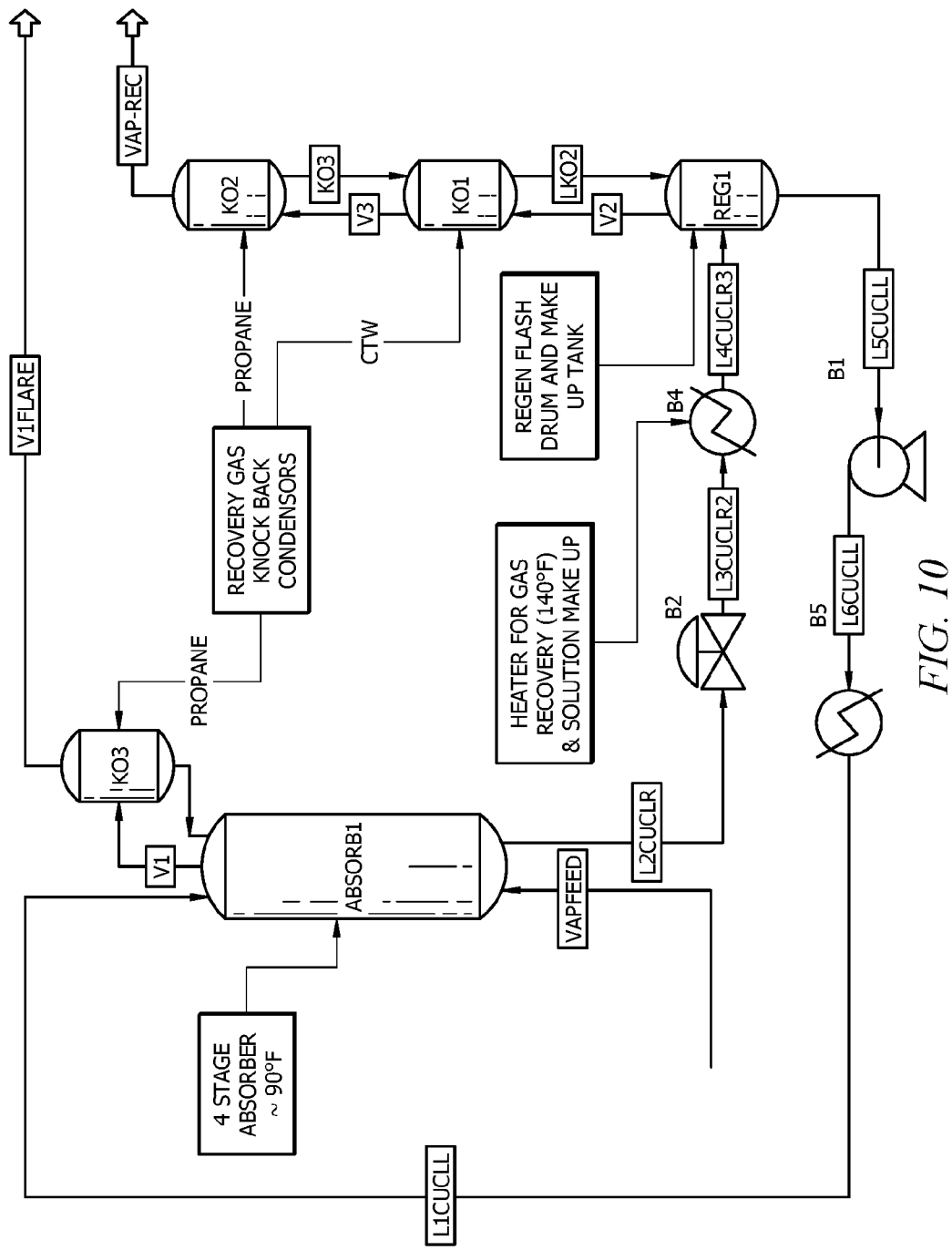
FIG. 10 illustrates a schematic of an embodiment of a simulated absorption system.

A computerized commercial process simulator was employed to generate an output from a model in accordance with the systems and/or processes disclosed herein. The model employed is illustrated at FIG. 10, wherein a gaseous stream, designated VAP FEED (e.g., the light gas stream disclosed herein) feeds to absorption reactor ASORB1. The output generated by the commercial process simulator is a material balance and a heat balance, shown in Table 3. The names designating the various streams listed in Table 3 correspond to streams illustrated in FIG. 10. In FIG. 10, ASORB1 is the absorption reactor, which is shown as a four stage absorber operating at 90° F.

TABLE 2

| Example | Lean Solvent Temp. (° F.) | Absorber top temperature (° F.) | REG1 temperature (° F.) | REG2 temperature (° F.) | Absorber pressure (psig) | REG1 temperature (psig) | REG2 temperature (psig) | Ethylene Recovery | Flow rate of circulation solvent (lb/hr) | Ethylene (wt %) | Ethane (wt %) | Nitrogen (wt %) | Hydrogen (wt %) | Isobutane (wt %) |
|---|---|---|---|---|---|---|---|---|---|---|---|---|---|---|
| 1 | 14 | 15 | 50 | 50 | 40 | 0 | 0 | 90% | 1704044 | 48.9% | 11.6% | 10.0% | 27.2% | 2.2% |
| 2 | 14 | 15 | 100 | 50 | 40 | 0 | 0 | 90% | 731337 | 57.7% | 13.0% | 11.1% | 18.9% | 2.3% |
| 3 | 14 | 15 | 150 | 50 | 40 | 0 | 0 | 90% | 344776 | 64.5% | 15.2% | 8.5% | 9.5% | 2.2% |
| 4 | 14 | 15 | 200 | 50 | 40 | 0 | 0 | 90% | 143736 | 77.5% | 16.3% | 2.1% | 3.3% | 0.8% |
| 5 | 50 | 50 | 50 | 50 | 40 | 0 | 0 | 90% | 672565 | 62.1% | 13.3% | 7.0% | 15.1% | 2.5% |
| 6 | 50 | 51 | 100 | 50 | 40 | 0 | 0 | 90% | 158735 | 81.9% | 11.2% | 1.8% | 4.1% | 1.0% |
| 7 | 50 | 53 | 150 | 50 | 40 | 0 | 0 | 90% | 53920 | 95.9% | 2.3% | 0.5% | 1.1% | 0.3% |
| 8 | 50 | 55 | 200 | 50 | 40 | 0 | 0 | 90% | 47785 | 96.5% | 1.9% | 0.4% | 1.0% | 0.3% |
| 9 | 100 | 100 | 100 | 50 | 40 | 0 | 0 | 90% | 921807 | 62.1% | 13.0% | 7.1% | 15.3% | 2.5% |
| 10 | 100 | 100 | 150 | 50 | 40 | 0 | 0 | 90% | 343211 | 78.4% | 9.5% | 3.2% | 7.1% | 1.9% |
| 11 | 100 | 101 | 200 | 50 | 40 | 0 | 0 | 90% | 88403 | 95.6% | 1.9% | 0.7% | 1.4% | 0.4% |
| 12 | 14 | 14 | 50 | 50 | 40 | 10 | 10 | N/A | | | | | | |
| 13 | 14 | 15 | 100 | 50 | 40 | 10 | 10 | 90% | 1321719 | 50.3% | 12.0% | 10.2% | 25.3% | 2.2% |
| 14 | 14 | 14 | 150 | 50 | 40 | 10 | 10 | 90% | 685442 | 56.2% | 13.3% | 10.6% | 17.7% | 2.3% |
| 15 | 14 | 15 | 200 | 50 | 40 | 10 | 10 | 90% | 420362 | 64.1% | 14.8% | 7.1% | 11.7% | 2.4% |
| 16 | 50 | 50 | 50 | 50 | 40 | 10 | 10 | 90% | 1367657 | 54.8% | 11.8% | 9.0% | 22.2% | 2.2% |
| 17 | 50 | 50 | 100 | 50 | 40 | 10 | 10 | 90% | 463945 | 66.9% | 14.6% | 5.1% | 11.1% | 2.3% |
| 18 | 50 | 51 | 150 | 50 | 40 | 10 | 10 | 90% | 121635 | 86.6% | 8.1% | 1.3% | 3.1% | 0.8% |
| 19 | 50 | 53 | 200 | 50 | 40 | 10 | 10 | 90% | 59272 | 95.6% | 2.5% | 0.5% | 1.2% | 0.3% |
| 20 | 100 | 100 | 100 | 50 | 40 | 10 | 10 | 90% | 1828349 | 54.8% | 11.6% | 9.0% | 22.3% | 2.2% |
| 21 | 100 | 100 | 150 | 50 | 40 | 10 | 10 | 90% | 880270 | 64.5% | 12.7% | 5.7% | 14.7% | 2.4% |
| 22 | 100 | 100 | 200 | 50 | 40 | 10 | 10 | 90% | 415884 | 77.5% | 9.6% | 2.3% | 8.4% | 2.1% |
| 23 | 14 | 15 | 50 | 50 | 60 | 0 | 0 | 90% | 858069 | 50.7% | 12.0% | 10.4% | 24.7% | 2.2% |
| 24 | 14 | 15 | 100 | 50 | 60 | 0 | 0 | 90% | 384021 | 58.5% | 13.9% | 11.4% | 13.7% | 2.5% |
| 25 | 14 | 15 | 150 | 50 | 60 | 0 | 0 | 90% | 159379 | 71.6% | 16.9% | 4.5% | 5.6% | 1.4% |
| 26 | 14 | 16 | 200 | 50 | 60 | 0 | 0 | 90% | 93956 | 82.2% | 12.7% | 1.7% | 2.8% | 0.7% |
| 27 | 50 | 50 | 50 | 50 | 60 | 0 | 0 | 90% | 296859 | 68.5% | 14.6% | 4.6% | 9.8% | 2.5% |
| 28 | 50 | 52 | 100 | 50 | 60 | 0 | 0 | 90% | 58613 | 93.9% | 3.4% | 0.7% | 1.6% | 0.4% |
| 29 | 50 | 55 | 150 | 50 | 60 | 0 | 0 | 90% | 51106 | 94.7% | 2.9% | 0.6% | 1.4% | 0.4% |
| 30 | 50 | 56 | 200 | 50 | 60 | 0 | 0 | 90% | 46744 | 95.3% | 2.6% | 0.5% | 1.3% | 0.3% |
| 31 | 100 | 100 | 100 | 50 | 60 | 0 | 0 | 90% | 428830 | 68.5% | 13.3% | 5.0% | 10.6% | 2.6% |
| 32 | 100 | 100 | 150 | 50 | 60 | 0 | 0 | 90% | 111161 | 90.5% | 4.1% | 1.5% | 3.0% | 0.9% |
| 33 | 100 | 102 | 200 | 50 | 60 | 0 | 0 | 90% | 63435 | 95.7% | 1.8% | 0.7% | 1.4% | 0.4% |
| 34 | 14 | 14 | 50 | 50 | 60 | 10 | 10 | N/A | | | | | | |
| 35 | 14 | 15 | 100 | 50 | 60 | 10 | 10 | 90% | 693610 | 52.5% | 12.5% | 10.6% | 22.1% | 2.3% |
| 36 | 14 | 15 | 150 | 50 | 60 | 10 | 10 | 90% | 346101 | 60.5% | 14.3% | 10.5% | 12.3% | 2.4% |
| 37 | 14 | 15 | 200 | 50 | 60 | 10 | 10 | 90% | 181196 | 71.0% | 16.3% | 4.4% | 6.7% | 1.6% |
| 38 | 50 | 50 | 50 | 50 | 60 | 10 | 10 | 90% | 669442 | 58.7% | 12.6% | 8.2% | 18.2% | 2.3% |
| 39 | 50 | 51 | 100 | 50 | 60 | 10 | 10 | 90% | 179196 | 75.0% | 15.2% | 2.6% | 5.8% | 1.4% |
| 40 | 50 | 52 | 150 | 50 | 60 | 10 | 10 | 90% | 57441 | 94.1% | 3.3% | 0.7% | 1.6% | 0.4% |
| 41 | 50 | 55 | 200 | 50 | 60 | 10 | 10 | 90% | 51482 | 94.8% | 2.9% | 0.5% | 1.4% | 0.4% |
| 42 | 100 | 100 | 100 | 50 | 60 | 10 | 10 | 90% | 896707 | 58.7% | 12.4% | 8.3% | 18.3% | 2.4% |
| 43 | 100 | 100 | 150 | 50 | 60 | 10 | 10 | 90% | 378813 | 71.8% | 12.1% | 4.1% | 9.6% | 2.4% |
| 44 | 100 | 100 | 200 | 50 | 60 | 10 | 10 | 90% | 130215 | 89.1% | 4.8% | 14.3% | 3.7% | 1.1% |

TABLE 3

| Substream: MIXED | L1CUCLL | L2CUCLR | L3CUCLR2 | L4CUCLR3 | L5CUCLL |
|---|---|---|---|---|---|
| Mole Flow lbmol/hr | | | | | |
| C2= | 1.949416 | 41.85801 | 41.85801 | 41.85801 | 1.949413 |
| C2 | 0.9764562 | 5.916248 | 5.916248 | 5.916248 | 0.9764532 |
| N2 | 1.15E−03 | 0.1711679 | 0.1711679 | 0.1711679 | 1.15E−03 |
| IC4 | 0.8615088 | 3.112527 | 3.112527 | 3.112527 | 0.8615092 |
| CUCL | 131.4402 | 131.4402 | 131.4402 | 131.4402 | 131.4402 |
| ANILINE | 580.5749 | 580.5749 | 580.5749 | 580.5749 | 580.5748 |
| NMP | 789.7864 | 789.7864 | 789.7864 | 789.7864 | 789.7864 |
| Mole Frac | | | | | |
| C2= | 1.29E−03 | 0.0269554 | 0.0269554 | 0.0269554 | 1.29E−03 |
| C2 | 6.49E−04 | 3.81E−03 | 3.81E−03 | 3.81E−03 | 6.49E−04 |
| N2 | 7.64E−07 | 1.10E−04 | 1.10E−04 | 1.10E−04 | 7.64E−07 |
| IC4 | 5.72E−04 | 2.00E−03 | 2.00E−03 | 2.00E−03 | 5.72E−04 |
| CUCL | 0.0873014 | 0.0846439 | 0.0846439 | 0.0846439 | 0.0873014 |
| ANILINE | 0.3856129 | 0.3738747 | 0.3738747 | 0.3738747 | 0.3856128 |
| NMP | 0.5245694 | 0.5086013 | 0.5086013 | 0.5086013 | 0.5245694 |

TABLE 3-continued

| | | | | | |
|---|---|---|---|---|---|
| Mass Flow lb/hr | | | | | |
| C2= | 54.68846 | 1174.274 | 1174.274 | 1174.274 | 54.68837 |
| C2 | 29.36169 | 177.8994 | 177.8994 | 177.8994 | 29.3616 |
| N2 | 0.0322059 | 4.795009 | 4.795009 | 4.795009 | 0.0322058 |
| IC4 | 50.07382 | 180.9106 | 180.9106 | 180.9106 | 50.07384 |
| CUCL | 13012.41 | 13012.41 | 13012.41 | 13012.41 | 13012.41 |
| ANILINE | 54067.97 | 54067.97 | 54067.97 | 54067.97 | 54067.96 |
| NMP | 78293.58 | 78293.58 | 78293.58 | 78293.58 | 78293.58 |
| Mass Frac | | | | | |
| C2= | 3.76E−04 | 7.99E−03 | 7.99E−03 | 7.99E−03 | 3.76E−04 |
| C2 | 2.02E−04 | 1.21E−03 | 1.21E−03 | 1.21E−03 | 2.02E−04 |
| N2 | 2.21E−07 | 3.26E−05 | 3.26E−05 | 3.26E−05 | 2.21E−07 |
| IC4 | 3.44E−04 | 1.23E−03 | 1.23E−03 | 1.23E−03 | 3.44E−04 |
| CUCL | 0.0894273 | 0.0885729 | 0.0885729 | 0.0885729 | 0.0894273 |
| ANILINE | 0.3715804 | 0.36803 | 0.36803 | 0.36803 | 0.3715804 |
| NMP | 0.5380702 | 0.532929 | 0.532929 | 0.532929 | 0.5380702 |
| Total Flow lbmol/hr | 1505.59 | 1552.86 | 1552.86 | 1552.86 | 1505.59 |
| Total Flow lb/hr | 145508 | 1.47E+05 | 1.47E+05 | 1.47E+05 | 1.46E+05 |
| Total Flow cuft/hr | 2000 | 2063.515 | 9563.191 | 13833 | 2058.304 |
| Temperature F. | 90 | 105.0961 | 95.53801 | 140 | 158 |
| Pressure psia | 117.6959 | 114.6959 | 25 | 25 | 25 |
| Vapor Frac | 0 | 0 | 0.020591 | 0.0297334 | 0 |
| Liquid Frac | 1 | 1 | 0.9794089 | 0.9702665 | 1 |
| Solid Frac | 0 | 0 | 0 | 0 | 0 |
| Enthalpy Btu/lbmol | −60439.71 | −58273.13 | −58273.13 | −56229.58 | −57622.43 |
| Enthalpy Btu/lb | −625.377 | −615.9475 | −615.9475 | −594.3472 | −596.2263 |
| Enthalpy Btu/hr | −9.10E+07 | −9.05E+07 | −9.05E+07 | −8.73E+07 | −8.68E+07 |
| Entropy Btu/lbmol-R | −112.3696 | −109.6524 | −109.5691 | −106.0242 | −107.4881 |
| Entropy Btu/lb-R | −1.162701 | −1.159027 | −1.158146 | −1.120676 | −1.112192 |
| Density lbmol/cuft | 0.75276 | 0.7525312 | 0.1623788 | 0.1122576 | 0.7314713 |
| Density lb/cuft | 72.75067 | 71.19494 | 15.36222 | 10.62039 | 70.69322 |
| Average MW | 96.64524 | 94.6073 | 94.6073 | 94.6073 | 96.64524 |
| Liq Vol 60 F. cuft/hr | 2474.029 | 2538.765 | 2538.765 | 2538.765 | 2474.029 |

| Substream: MIXED | L6CUCLL | LKO1 | LKO2 | LKO3 | V1 |
|---|---|---|---|---|---|
| Mole Flow lbmol/hr | | | | | |
| C2= | 1.949413 | 2.02E−04 | 4.41E−03 | 9.89E−04 | 3.172776 |
| C2 | 0.9764532 | 6.17E−04 | 8.14E−04 | 2.10E−04 | 5.654325 |
| N2 | 1.15E−03 | 8.35E−06 | 8.99E−07 | 6.78E−08 | 7.187729 |
| IC4 | 0.8615092 | 2.14E−04 | 2.23E−03 | 1.08E−03 | 0.1670439 |
| CUCL | 131.4402 | 1.50E−13 | 2.85E−13 | 0 | 1.50E−13 |
| ANILINE | 580.5748 | 2.47E−03 | 0.2059512 | 0.0219362 | 2.48E−03 |
| NMP | 789.7864 | 2.38E−03 | 0.1961199 | 9.42E−03 | 2.38E−03 |
| Mole Frac | | | | | |
| C2= | 1.29E−03 | 0.0343637 | 0.0107758 | 0.0294004 | 0.1960108 |
| C2 | 6.49E−04 | 0.1047838 | 1.99E−03 | 6.25E−03 | 0.3493185 |
| N2 | 7.64E−07 | 1.42E−03 | 2.19E−06 | 2.02E−06 | 0.4440506 |
| IC4 | 5.72E−04 | 0.0362971 | 5.44E−03 | 0.032152 | 0.0103198 |
| CUCL | 0.0873014 | 2.54E−11 | 6.97E−13 | 0 | 9.24E−15 |
| ANILINE | 0.3856128 | 0.4198489 | 0.5029009 | 0.6521121 | 1.53E−04 |
| NMP | 0.5245694 | 0.4032882 | 0.4788945 | 0.2800845 | 1.47E−04 |
| Mass Flow lb/hr | | | | | |
| C2= | 54.68837 | 5.68E−03 | 0.1238009 | 0.027745 | 89.00829 |
| C2 | 29.3616 | 0.0185606 | 0.0244775 | 6.32E−03 | 170.0235 |
| N2 | 0.0322058 | 2.34E−04 | 2.52E−05 | 1.90E−06 | 201.3533 |
| IC4 | 50.07384 | 0.0124277 | 0.129461 | 0.0628636 | 9.709158 |

TABLE 3-continued

|  | | | | | |
|---|---|---|---|---|---|
| CUCL | 13012.41 | 1.48E−11 | 2.83E−11 | 0 | 1.48E−11 |
| ANILINE | 54067.96 | 0.2303272 | 19.17989 | 2.042886 | 0.2311832 |
| NMP | 78293.58 | 0.2355062 | 19.44187 | 0.9339974 | 0.2358215 |
| Mass Frac | | | | | |
| | | | | | |
| C2 = | 3.76E−04 | 0.0112959 | 3.18E−03 | 9.03E−03 | 0.1891534 |
| C2 | 2.02E−04 | 0.0369193 | 6.29E−04 | 2.06E−03 | 0.3613207 |
| N2 | 2.21E−07 | 4.66E−04 | 6.47E−07 | 6.18E−07 | 0.4279003 |
| IC4 | 3.44E−04 | 0.0247203 | 3.33E−03 | 0.0204513 | 0.0206331 |
| CUCL | 0.0894273 | 2.95E−11 | 7.26E−13 | 0 | 3.15E−14 |
| ANILINE | 0.3715804 | 0.4581486 | 0.4930622 | 0.6646093 | 4.91E−04 |
| NMP | 0.5380702 | 0.4684502 | 0.4997972 | 0.3038561 | 5.01E−04 |
| Total Flow lbmol/hr | 1505.59 | 5.89E−03 | 0.4095263 | 0.0336387 | 16.18674 |
| Total Flow lb/hr | 1.46E+05 | 0.5027346 | 38.89952 | 3.073815 | 470.5613 |
| Total Flow cuft/hr | 2058.521 | 8.16E−03 | 0.6204605 | 0.04765 | 825.9148 |
| Temperature F. | 158.2431 | −20 | 90 | −20 | 96.94405 |
| Pressure psia | 118.6959 | 114.6959 | 24.9 | 24.8 | 114.6959 |
| Vapor Frac | 0 | 0 | 0 | 0 | 1 |
| Liquid Frac | 1 | 1 | 1 | 1 | 0 |
| Solid Frac | 0 | 0 | 0 | 0 | 0 |
| Enthalpy Btu/lbmol | −57585.8 | −49592.05 | −47471.61 | −28177.63 | −8659.402 |
| Enthalpy Btu/lb | −595.8472 | −581.0902 | −499.7715 | −308.3662 | −297.8729 |
| Enthalpy Btu/hr | −8.67E+07 | −292.1342 | −19440.87 | −947.8608 | −1.40E+05 |
| Entropy Btu/lbmol-R | −107.4788 | −111.4813 | −112.727 | −110.4079 | −19.64671 |
| Entropy Btu/lb-R | −1.112096 | −1.306271 | −1.186767 | −1.208266 | −0.6758228 |
| Density lbmol/cuft | 0.731394 | 0.7221323 | 0.6600361 | 0.7059546 | 0.0195985 |
| Density lb/cuft | 70.68575 | 61.62902 | 62.6946 | 64.50811 | 0.5697456 |
| Average MW | 96.64524 | 85.34311 | 94.98663 | 91.37714 | 29.0708 |
| Liq Vol 60 F. cuft/hr | 2474.029 | 8.78E−03 | 0.6165612 | 0.0501975 | 18.42872 |

| Substream: MIXED | V1FLARE | V2 | V3 | VAP-REC | VAPFEED |
|---|---|---|---|---|---|
| Mole Flow lbmol/hr | | | | | |
| | | | | | |
| C2 = | 3.172573 | 39.91302 | 39.9096 | 39.90861 | 43.08116 |
| C2 | 5.653708 | 4.940621 | 4.940017 | 4.939807 | 10.5935 |
| N2 | 7.187721 | 0.1700194 | 0.1700186 | 0.1700185 | 7.357739 |
| IC4 | 0.1668301 | 2.253242 | 2.252096 | 2.251014 | 2.417848 |
| CUCL | 4.78E−22 | 2.85E−13 | 2.86E−24 | 0 | 0 |
| ANILINE | 9.19E−06 | 0.20608 | 0.022065 | 1.29E−04 | 0 |
| NMP | 3.17E−06 | 0.1961404 | 9.44E−03 | 2.06E−05 | 0 |
| Mole Frac | | | | | |
| | | | | | |
| C2 = | 0.1960697 | 0.8371173 | 0.843697 | 0.8442764 | 0.6789755 |
| C2 | 0.3494075 | 0.1036223 | 0.104433 | 0.1045028 | 0.1669576 |
| N2 | 0.4442117 | 3.57E−03 | 3.59E−03 | 3.60E−03 | 0.1159608 |
| IC4 | 0.0103103 | 0.0472584 | 0.0476097 | 0.0476207 | 0.0381062 |
| CUCL | 2.95E−23 | 5.99E−15 | 6.04E−26 | 0 | 0 |
| ANILINE | 5.68E−07 | 4.32E−03 | 4.66E−04 | 2.73E−06 | 0 |
| NMP | 1.96E−07 | 4.11E−03 | 2.00E−04 | 4.36E−07 | 0 |
| Mass Flow lb/hr | | | | | |
| | | | | | |
| C2 = | 89.00261 | 1119.71 | 1119.614 | 1119.587 | 1208.589 |
| C2 | 170.005 | 148.5627 | 148.5445 | 148.5382 | 318.5427 |
| N2 | 201.3531 | 4.762835 | 4.762812 | 4.76281 | 206.1159 |
| IC4 | 9.69673 | 130.9661 | 130.8995 | 130.8366 | 140.5336 |
| CUCL | 4.73E−20 | 2.83E−11 | 2.83E−22 | 0 | 0 |
| ANILINE | 8.56E−04 | 19.19188 | 2.054883 | 0.0120247 | 0 |
| NMP | 3.14E−04 | 19.4439 | 0.9360284 | 2.04E−03 | 0 |
| Mass Frac | | | | | |
| | | | | | |
| C2 = | 0.1893437 | 0.7761549 | 0.7958521 | 0.797575 | 0.645 |
| C2 | 0.3616676 | 0.1029799 | 0.1055895 | 0.1058162 | 0.17 |
| N2 | 0.4283574 | 3.30E−03 | 3.39E−03 | 3.39E−03 | 0.11 |
| IC4 | 0.0206287 | 0.0907823 | 0.0930468 | 0.0932058 | 0.075 |
| CUCL | 1.01E−22 | 1.96E−14 | 2.01E−25 | 0 | 0 |

TABLE 3-continued

| | | | | | |
|---|---|---|---|---|---|
| ANILINE | 1.82E−06 | 0.0133033 | 1.46E−03 | 8.57E−06 | 0 |
| NMP | 6.69E−07 | 0.013478 | 6.65E−04 | 1.46E−06 | 0 |
| Total Flow lbmol/hr | 16.18085 | 47.67913 | 47.30324 | 47.2696 | 63.45025 |
| Total Flow lb/hr | 470.0586 | 1442.638 | 1406.812 | 1403.738 | 1873.781 |
| Total Flow cuft/hr | 634.7071 | 12547.34 | 11089.96 | 8812.544 | 1155.656 |
| Temperature F. | −20 | 158 | 90 | −20 | 0 |
| Pressure psia | 114.6959 | 25 | 24.9 | 24.8 | 226.6959 |
| Vapor Frac | 1 | 1 | 1 | 1 | 0.9823996 |
| Liquid Frac | 0 | 0 | 0 | 0 | 0.0176004 |
| Solid Frac | 0 | 0 | 0 | 0 | 0 |
| Enthalpy Btu/lbmol | −9795.256 | 13137.72 | 12629.88 | 11470.01 | 5793.013 |
| Enthalpy Btu/lb | −337.1825 | 434.201 | 424.6725 | 386.242 | 196.1639 |
| Enthalpy Btu/hr | −1.59E+05 | 6.26E+05 | 5.97E+05 | 5.42E+05 | 3.68E+05 |
| Entropy Btu/lbmol-R | −21.92954 | −18.274 | −19.22263 | −21.55552 | −25.0739 |
| Entropy Btu/lb-R | −0.7548814 | −0.603955 | −0.6463497 | −0.7258623 | −0.8490563 |
| Density lbmol/cuft | 0.0254934 | 3.80E−03 | 4.27E−03 | 5.36E−03 | 0.0549041 |
| Density lb/cuft | 0.7405913 | 0.1149756 | 0.1268545 | 0.1592887 | 1.6214 |
| Average MW | 29.05031 | 30.25722 | 29.74029 | 29.69643 | 29.5315 |
| Liq Vol 60 F. cuft/hr | 18.41994 | 65.35257 | 64.78621 | 64.73601 | 83.15566 |

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent . . . 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the disclosed inventive subject matter. The discussion of a reference in the disclosure is not an admission that it is prior art, especially any reference that has a publication date after the priority date of this application. The disclosure of all patents, patent applications, and publications cited in the disclosure are hereby incorporated by reference, to the extent that they provide exemplary, procedural or other details supplementary to the disclosure.

We claim:

1. A process comprising
contacting ethylene and a polymerization catalyst in a first loop slurry reactor and in a second loop slurry reactor connected in series with the first loop slurry reactor, under suitable reaction conditions to yield a polymerization product stream flowing from the second loop slurry reactor, wherein the polymerization product stream comprises a bimodal polymer;
separating a as stream from the polymerization product stream, wherein the gas stream comprises unreacted ethylene and ethane;
separating, using an absorption solvent system at a temperature in a range of from about 40° F. to about 110° F., at least one gaseous component from the gas stream to form a recycle stream comprising unreacted ethylene and a waste stream comprising ethane, wherein absorption solvent system comprises copper chloride, aniline, and N-methylpyrrolidone; and
recycling the unreacted ethylene of the recycle stream to the first loop slurry reactor, the second loop slurry reactor, or both the first loop slurry reactor and the second loop slurry reactor.

2. The process of claim 1, wherein the bimodal polymer comprises a high molecular weight polymer and a low molecular weight polymer.

3. The process of claim 2, wherein the high molecular weight polymer has a low density, and wherein the low molecular weight polymer has a high density.

4. The process of claim 1, wherein the polymerization catalyst is selected from a Ziegler Natta catalyst, a Ziegler catalyst, a chromium catalyst, a chromium oxide catalyst, a chromocene catalyst, a metallocene catalyst, a nickel catalyst, or combinations thereof.

5. The process of claim 1, wherein the at least one gaseous component comprises the unreacted ethylene, optionally isobutane, and optionally unreacted comonomer.

6. The process of claim 1, wherein separating, using an absorption solvent system at a temperature in a range of from about 40° F. to about 110° F., at least one gaseous component from the gas stream comprises:
contacting the gas stream with the absorption solvent system, wherein at least a portion of the unreacted ethylene from the gas stream is absorbed by the absorption solvent system, wherein at least a portion of the ethane is unabsorbed by the absorption solvent system;
recovering the unreacted ethylene from the absorption solvent system in the recycle stream; and
recovering the unabsorbed ethane in the waste stream.

7. The process of claim 1, further comprising:
removing at least a portion of elemental oxygen or oxygen-containing compounds from the gas stream prior to separating the at least one gaseous component from the gas stream.

8. The process of claim 1, wherein separating a gas stream from the polymerization product stream comprises:
routing the polymerization product stream to a separator selected from a distillation column, a flash tank, a filter, a membrane, a reactor, an absorbent, an adsorbent, a molecular sieve, or combinations thereof.

9. The process of claim 1, further comprising:
combusting ethane of the waste stream.

10. A process comprising:
contacting ethylene and a polymerization catalyst in a first loop slurry reactor and in a second loop slurry reactor connected in series with the first loop slurry reactor, under suitable reaction conditions to yield a polymerization product stream flowing from the second loop slurry reactor, wherein the polymerization product stream comprises a bimodal polymer;
separating a gas stream from the polymerization product stream, wherein the gas stream comprises unreacted ethylene and ethane;
separating, using an absorption solvent system at a temperature in a range of from about 40° F. to about 110° F., at least gaseous component from the gas stream to form a recycle stream comprising unreacted ethylene and a waste stream comprising ethane; and
recycling the unreacted ethylene of the recycle stream to the first loop slurry reactor, the second loop slurry reactor, or both the first loop slurry reactor and the second loop slurry reactor, wherein separating, using an absorption solvent system at a temperature in a range of from about 40° F. to about 110° F., at least one gaseous component from the gas stream comprises:
contacting the gas stream with the absorption solvent system, wherein at least a portion of the unreacted ethylene from the gas stream is absorbed by the absorption solvent system, wherein at least a portion of the ethane is unabsorbed by the absorption solvent system;
recovering the unreacted ethylene from the absorption solvent system in the recycle stream; and
recovering the unabsorbed ethane in the waste stream; and
wherein contacting the gas stream with the absorption solvent system occurs at a pressure in a range of frown about 40 psig to about 60 psig, and wherein recovering the unreacted ethylene from the absorption solvent system in the recycle stream comprises depressurizing the absorption solvent system utilizing pressure swing absorption.

11. The process of claim 10, wherein the absorption solvent system comprises copper chloride, aniline, and N-methylpyrrolidone.

12. The process of claim 10, wherein the bimodal polymer comprises a high molecular weight polymer having a low density and a low molecular weight polymer having a high density and wherein the polymerization catalyst is selected from a Ziegler Natta catalyst, a Ziegler catalyst, a chromium catalyst, a chromium oxide catalyst, a chromocene catalyst, a metallocene catalyst, a nickel catalyst, or combinations thereof.

13. A process comprising:
contacting ethylene and a polymerization catalyst in a first loop slurry reactor and in a second loop slurry reactor connected in series with the first loop slurry reactor, under suitable reaction conditions to yield a polymerization product stream flowing from the second loop slurry reactor, wherein the polymerization product stream comprises a bimodal polymer;
separating a gas stream from the polymerization product stream, wherein the gas stream comprises unreacted ethylene and ethane;
separating, using an absorption solvent system at a temperature in a range of from about 40° F. to about 110° F., at least on gaseous component horn the gas stream to form a recycle stream comprising unreacted ethylene and a waste stream comprising ethane; and
recycling the unreacted ethylene of the recycle stream to the first loop slurry reactor, the second loop slurry reactor, or both the first loop slurry reactor and the second loop slurry reactor,
wherein separating, using an absorption solvent system at a temperature in a range of from about 40° F. to about 110° F., at least one gaseous component from the gas stream comprises:
contacting the gas stream with the absorption solvent system at a pressure in a range of from about 40 psig to about 60 psig, wherein at least a portion of the unreacted ethylene from the gas stream is absorbed by the absorption solvent system, wherein at least a portion of the ethane is unabsorbed by the absorption solvent system;
introducing a complexed stream comprising a complex of the absorption solvent system and unreacted ethylene into a solvent regenerator;
depressurizing the solvent regenerator to a pressure in a range of from about 0 psig to about 10 psig; and
recovering the recycle stream from the solvent regenerator.

14. The process of claim 13, wherein the absorption solvent system comprises copper chloride, aniline, and N-methylpyrrolidone.

15. The process of claim 13, wherein the bimodal polymer comprises a high molecular weight polymer having a low density and a low molecular weight polymer having a high density and wherein the polymerization catalyst is selected from a Ziegler Natta catalyst, a Ziegler catalyst, a chromium catalyst, a chromium oxide catalyst, a chromocene catalyst, a metallocene catalyst, a nickel catalyst, or combinations thereof.

16. A process comprising:
contacting ethylene and a polymerization catalyst in a first loop slurry reactor and in a second loop slurry reactor connected in series with the first loop slurry reactor, under suitable reaction conditions to yield a polymerization product stream flowing from the second loop slurry reactor, wherein the polymerization product stream comprises a bimodal polymer;

separating a as stream from the polymerization product stream, wherein the gas stream comprises unreacted ethylene and ethane;

separating, using an absorption solvent system at a temperature in a range of from about 40° F. to about 110° F., at least one gaseous component from the gas stream to form a recycle stream comprising unreacted ethylene and a waste stream comprising ethane; and recycling the unreacted ethylene of the recycle stream to the first loop slurry reactor, the second loop slurry reactor, or both the first loop slurry reactor and the second loop slurry reactor, and further comprising:

converting ethane of the waste stream into ethylene; and recycling the ethylene obtained by converting ethane to the first loop slurry reactor, the second loop slurry reactor, or both the first loop slurry reactor and the second loop slurry reactor.

17. The process of claim 16, wherein the absorption solvent system comprises copper chloride, aniline, and N-methylpyrrolidone.

18. The process of claim 16, wherein the bimodal polymer comprises a high molecular weight polymer having a low density and a low molecular weight polymer having a high density and wherein the polymerization catalyst is selected from a Ziegler Natta catalyst, a Ziegler catalyst, a chromium catalyst, a chromium oxide catalyst, a chromocene catalyst, a metallocene catalyst, a nickel catalyst, or combinations thereof.

19. A polyethylene production system, comprising:
a first loop slurry reactor;
a second loop slurry reactor connected in series with the first loop slurry reactor, wherein the first loop slurry reactor and the second loop slurry reactor are configured to contact ethylene with a polymerization catalyst under suitable reaction conditions to yield a polymerization product stream flowing from the second loop slurry reactor, wherein the polymerization product stream comprises a bimodal polymer;
a first separator configured to receive the polymerization product stream, to recover the bimodal polymer in a polymer stream, and to recover unreacted ethylene and ethane in a gas stream; and
one or more absorption reactors configured to receive the gas stream, wherein the one or more absorption reactors contains an absorption solvent system which is at a temperature in a range of from about 40° F. to about 110° F., wherein at least a portion of the unreacted ethylene received from the gas stream is absorbed by the absorption solvent system, wherein at least a portion of the ethane received from the gas stream is unabsorbed by the absorption solvent system, and wherein the absorption solvent system comprises copper chloride, aniline, and N-methylpyrrolidone.

20. The system of claim 19, wherein the bimodal polymer comprises a high molecular weight polymer having a low density and a low molecular weight polymer having a high density and wherein the polymerization catalyst is selected from a Ziegler Natta catalyst, a Ziegler catalyst, a chromium catalyst, a chromium oxide catalyst, a chromocene catalyst, a metallocene catalyst, a nickel catalyst, or combinations thereof.

21. A polyethylene production system, comprising:
a first loop slurry reactor;
a second loop slurry reactor connected in series with the first loop slurry reactor, wherein the first loop slurry reactor and the second loop slurry reactor are configured to contact ethylene with a polymerization catalyst under suitable reaction condition to yield a polymerization product stream flowing from the second loop slurry reactor, wherein the polymerization product stream comprises a bimodal polymer;
a first separator configured to receive the polymerization product stream, to recover the bimodal polymer in a polymer stream, and to recover unreacted ethylene and ethane in a gas stream; and
one or more absorption reactors configured to receive the gas stream, wherein the one or more absorption reactors contains an absorption solvent system which is at a temperature in a range of from about 40° F. to about 110° F., wherein at least a portion of the unreacted ethylene received from the gas stream is absorbed by the absorption solvent system, wherein at least a portion of the ethane received from the gas stream is unabsorbed by the absorption solvent system,
wherein the one or more absorption reactors operate with pressure swing absorption to recover the unreacted ethylene, the system further comprising:
a recycle stream comprising unreacted ethylene recovered from the one or more absorption reactors, wherein the recycle stream flows unreacted ethylene to the first loop slurry reactor, the second loop slurry reactor, or both the first loop slurry reactor and the second loop slurry reactor, and
a waste stream comprising the unabsorbed ethane recovered from the one or more absorption reactors.

22. The system of claim 21, wherein the absorption solvent system comprises copper chloride, aniline, and N-methylpyrrolidone.

23. The system of claim 21, further comprising:
a processing device configured to combust ethane received from the waste stream or configured to convert ethane received from the waste stream to ethylene.

24. The system of claim 21, wherein the bimodal polymer comprises a high molecular weight polymer having a low density and a low molecular weight polymer having a high density and wherein the polymerization catalyst is selected from a Ziegler Natta catalyst, a Ziegler catalyst, a chromium catalyst, a chromium oxide catalyst, a chromocene catalyst, a metallocene catalyst, a nickel catalyst, or combinations thereof.

25. A polyethylene production system, comprising:
a first loop slurry reactor;
a second loop slurry reactor connected in series with the first loop slurry reactor, wherein the first loop slurry reactor and the second loop slurry reactor are configured to contact ethylene with a polymerization catalyst under suitable reaction condition to yield a polymerization product stream flowing from the second loop slurry reactor, wherein the polymerization product stream comprises a bimodal polymer;
a first separator configured to receive the polymerization product stream, to recover the bimodal polymer in a polymer stream, and to recover unreacted ethylene and ethane in a gas stream; and
one or more absorption reactors configured to receive the gas stream, wherein the one or more absorption reactors contains an absorption solvent system which is at a temperature in a range of from about 40° F. to about 110° F., wherein at least a portion of the unreacted ethylene received from the gas stream is absorbed by the absorption solvent system, wherein at least a portion of the ethane received from the gas stream is unabsorbed by the absorption solvent system, and further comprising:
  a complexed stream flowing from the one or more absorption reactors, wherein the complexed stream comprises a complex of the absorption solvent system and unreacted ethylene;
a solvent regenerator configured to receive the complexed stream and to recover the unreacted ethylene from the complex; and
  a recycle stream comprising the unreacted ethylene recovered from the complex,
  wherein the unreacted ethylene recovered from the complex is recycled to the first loop slurry reactor, the second loop slurry reactor, or both the first loop slurry reactor and the second loop slurry reactor via the recycle stream.

26. The system of claim 25, wherein the complexed stream further comprises ethane, the system further comprising:
  a waste gas stream comprising the unabsorbed ethane recovered by the solvent regenerator from the complexed stream.

27. The system of claim 26, further comprising
  a processing device configured to combust ethane received from the waste stream or configured to convert ethane received from the waste stream to ethylene.

28. The system of claim 25, wherein the absorption solvent system comprises copper chloride, aniline, and N-methylpyrrolidone.

29. The system of claim 25, wherein the bimodal polymer comprises a high molecular weight polymer having a low density and a low molecular weight polymer having a high density and wherein the polymerization catalyst is selected from a Ziegler Natta catalyst, a Ziegler catalyst, a chromium catalyst, a chromium oxide catalyst, a chromocene catalyst, a metallocene catalyst, a nickel catalyst, or combinations thereof.

30. A process comprising:
  contacting ethylene and a polymerization catalyst in a first loop slurry reactor and in a second loop slurry reactor connected in series with the first loop slurry reactor, under suitable reaction conditions to yield a polymerization product stream flowing from the second loop slurry reactor, wherein the polymerization product stream comprises a bimodal polymer,
  separating a gas stream from the polymerization product stream, wherein the gas stream comprises unreacted ethylene and ethane;
  separating, using an absorption solvent system comprising copper chloride, aniline, and N-methylpyrrolidone, at least one gaseous component from the gas stream to form a recycle stream comprising unreacted ethylene and a waste stream comprising ethane; and
  recycling the unreacted ethylene of the recycle stream to the first loop slurry reactor, the second loop slurry reactor, or both the first loop slurry reactor and the second loop slurry reactor.

* * * * *